United States Patent [19]
Yamafuji et al.

[11] Patent Number: 5,482,855
[45] Date of Patent: Jan. 9, 1996

[54] TASTE SENSING SYSTEM USING ARTIFICIAL LIPID MEMBRANES

[75] Inventors: Kaoru Yamafuji, 1-6-21, Kusagae, Chuo-ku; Kiyoshi Toko, 1-25-2, Miwadai, Higashi-ku; Kenshi Hayashi, 2412 Ooazatajiri, Nishi-ku, all of Fukuoka-shi, Fukuoka-ken, Japan

[73] Assignees: Anritsu Corporation, Tokyo; Kaoru Yamafuji, Fukoka; Kiyoshi Toko, Fukoka; Kenshi Hayashi, Fukoka, all of Japan

[21] Appl. No.: 28,683

[22] Filed: Mar. 8, 1993

Related U.S. Application Data

[63] Continuation of Ser. No. 555,163, Jul. 19, 1990, abandoned.

[30] Foreign Application Priority Data

Jul. 24, 1989 [JP] Japan ................................ 1-190819

[51] Int. Cl.$^6$ ............................. C12M 1/34; G01N 27/00
[52] U.S. Cl. ...................... 435/287.1; 436/501; 436/503; 204/153.1; 204/403; 204/415; 324/446; 324/450; 422/98
[58] Field of Search .............................. 422/98; 204/415; 436/503

[56] References Cited

U.S. PATENT DOCUMENTS

| | | | |
|---|---|---|---|
| H201 | 1/1987 | Yager | 436/151 |
| 4,490,216 | 12/1984 | McConnell | 204/1 T |
| 4,637,861 | 1/1987 | Krull et al. | 204/1 T |
| 4,661,235 | 4/1987 | Krull et al. | 204/414 |

FOREIGN PATENT DOCUMENTS 0158834  10/1985  European Pat. Off. ..... G01N 27/100

OTHER PUBLICATIONS

Agric. Biol. Chem. 50(11), pp. 1709 to 2714 (1986).
C. Pfaffman, Handbook of Physiology, Section 1, Neurophysiology vol. 1, ed. by J. Field, American Physiological Society, Washington, D.C., 1959, p. 507.
Proceedings of the 5th Sensor Symposium, 1985, pp. 231–236 Kiyoshi Toko et al.
Agri. Biol. Chem., 50(11), pp. 2709–2714, 1986 Satoru Iiyama et al.
Membrane, 12(4), pp. 231–237, 1987, Satoru Iiyama et al.
Technical Digest of the 7th Sensor Symposium, 1988; pp. 127–130; Kiyoshi Toko et al.
Agric. Biol. Chem., 53(3), pp. 675–681, 1989; Satoru Iiyama et al.
Sensors and Actuators, 16(1989), pp. 25–42; K. Hayashi et al.
Sensors and Materials, 1–6(1989), pp. 321–334 K. Hayashi et al.
Japanese Journal of Applied Physics vol. 28, No. 8, Aug., 1989, pp. 1507–1512; Kenshi Hayashi et al.
Technical Digest of the 9th Sensor Symposium, 1990, pp. 193–196; Kiyoshi Toko et al.

(List continued on next page.)

Primary Examiner—David A. Redding
Attorney, Agent, or Firm—Frishauf, Holtz, Goodman, Langer & Chick

[57] ABSTRACT

A taste sensor has a lipid membrane including lipid molecules and a membrane-forming material for accommodating at least some of the lipid molecules on its surface. The lipid membrane induces a change in electrical characteristics, when a taste substance reacts with the surface of the lipid membrane. A signal processing unit receives a signal indicating a change in electrical characteristics induced by the taste sensor and generates data for determining the taste of the taste substance.

14 Claims, 22 Drawing Sheets

OTHER PUBLICATIONS

Patent Abstracts of Japan, Unexamined Applications, vol. 13, No. 47 (P-822) [3395], Feb. 3, 1989, P. Field, The Patent Office Japanese Government.

Kurihara, K.: "Receptor mechanisms of taste and olfaction, Faculty of Pharmaceutical Sciences", Hokkaido University. 60 (7) 1991, pp. 682–689.

Biophys. J., vol. 59, Jun. 1991, pp. 1218–1234.

Biochemistry 1987, 26, pp. 6141–6145.

Sensors and Actuators, B, 2 (1990) 205–213.

C–II, vol. J74–C–II, No. 5, pp. 434–442 (1991): "Multi–Channel Taste Sensor with Artificial Lipid Membranes" & Partial Translation of p. 439.

Technical Digest of 10th Sensor Symposium, 1991, pp. 173–176.

Transducers '87 pp. 793–796 K. Toko, S. Iiyama et al.

Yamanaka, M. et al. Technical Digest of the 9th Sensor Symposium, 1990, pp. 193–196.

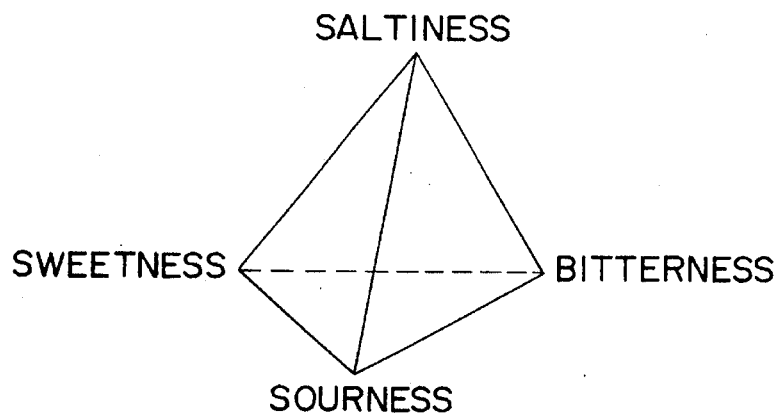
F I G. 3
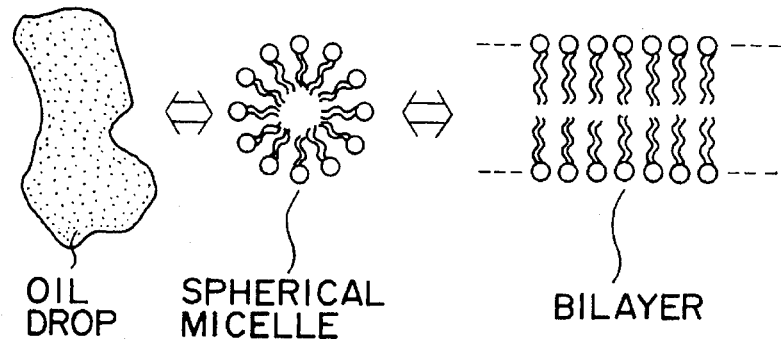
F I G. 4
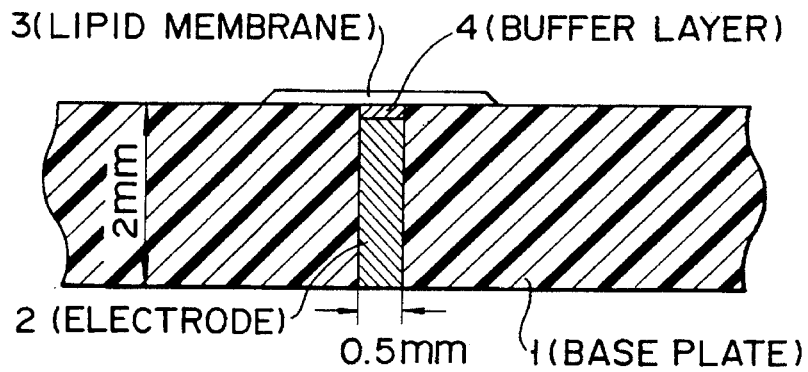
F I G. 5

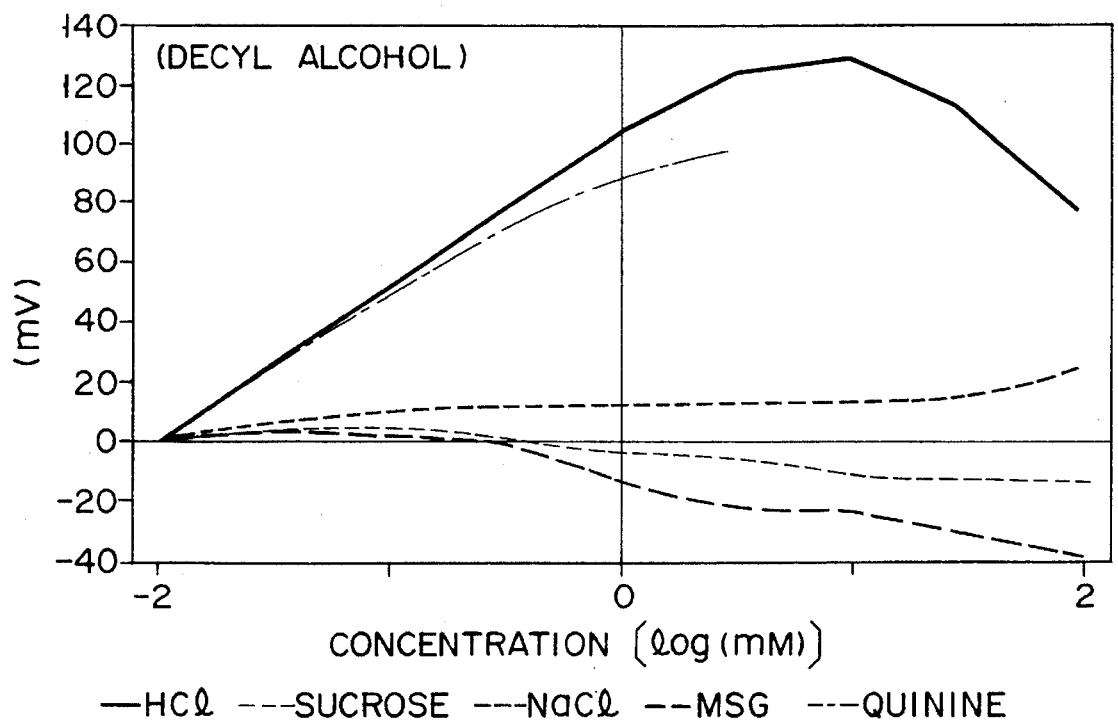
F I G. 10
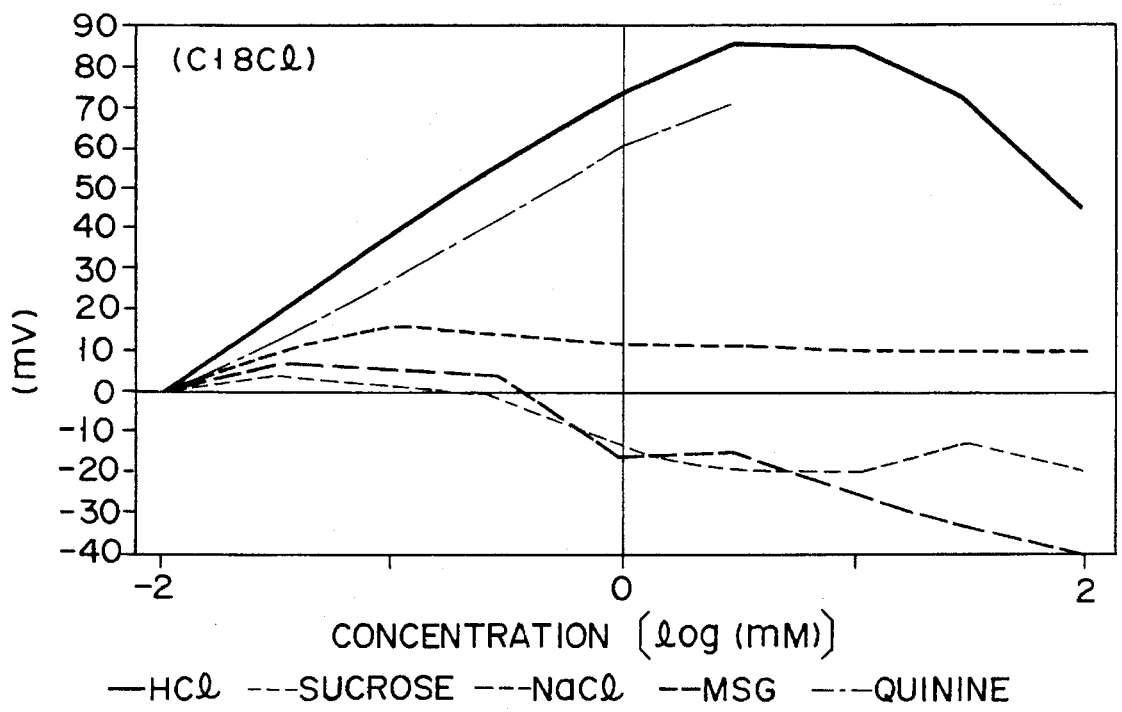
F I G. 11

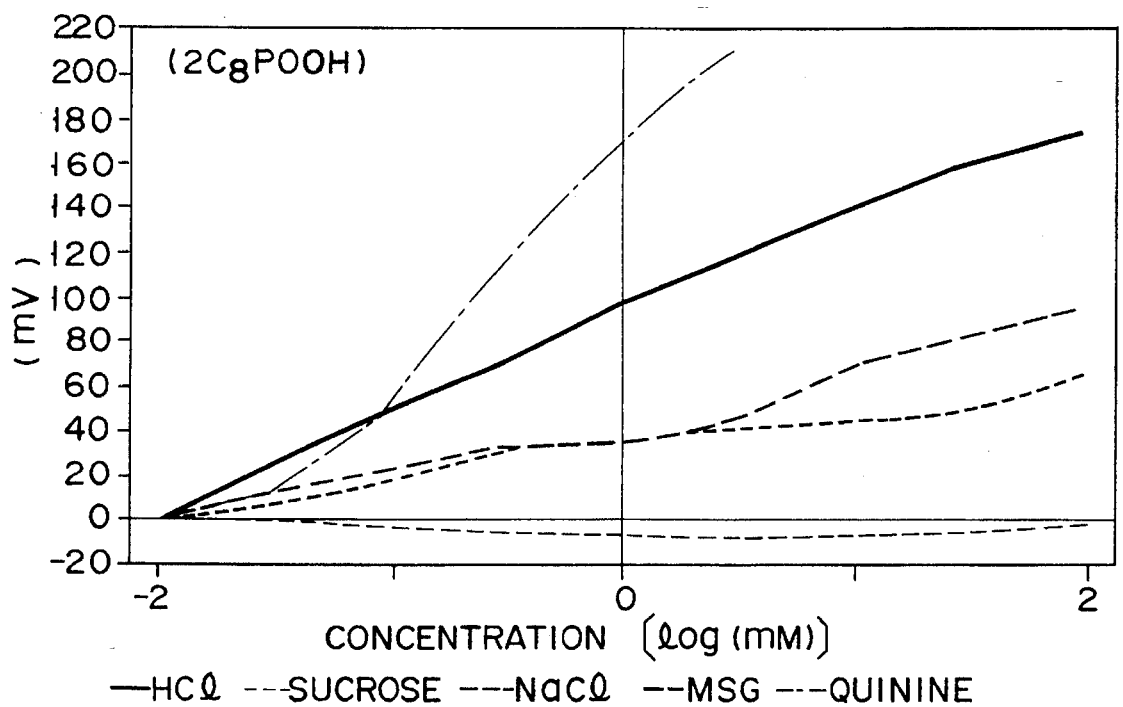
F I G. 12
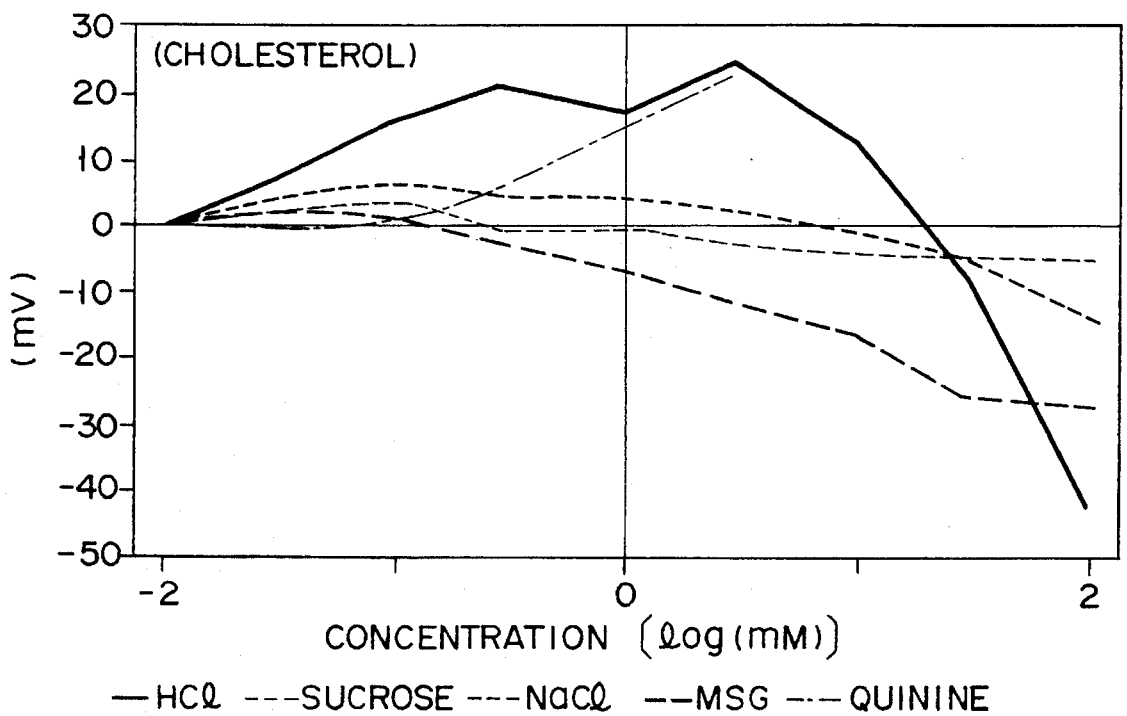
F I G. 13

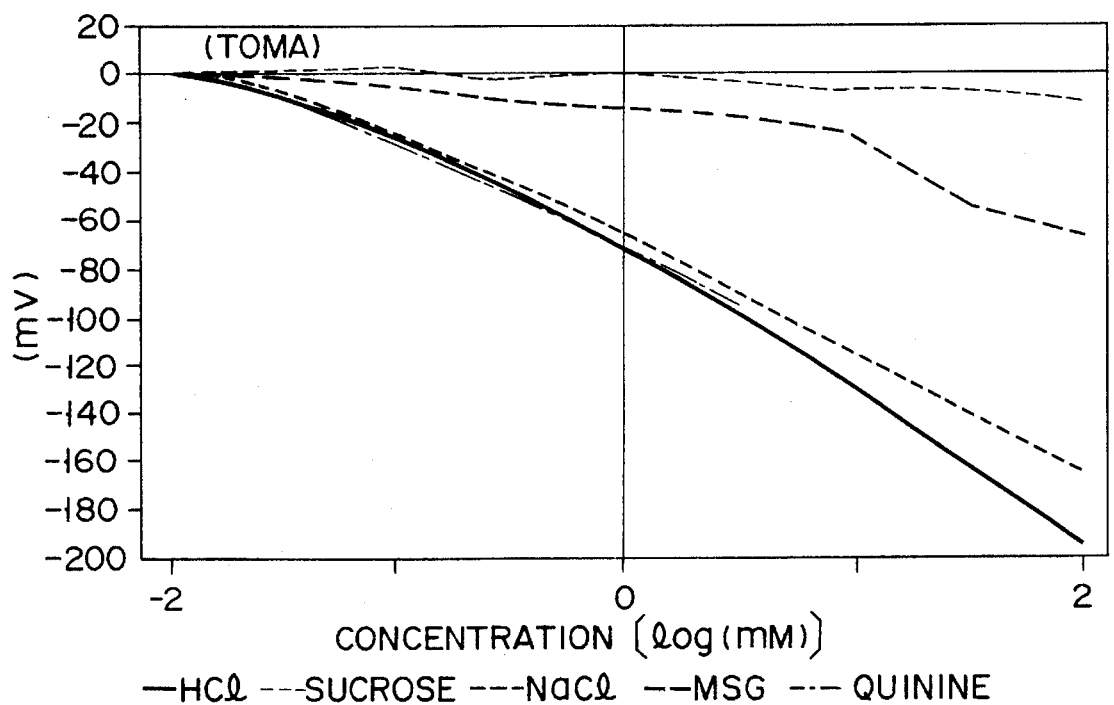
F I G. 14
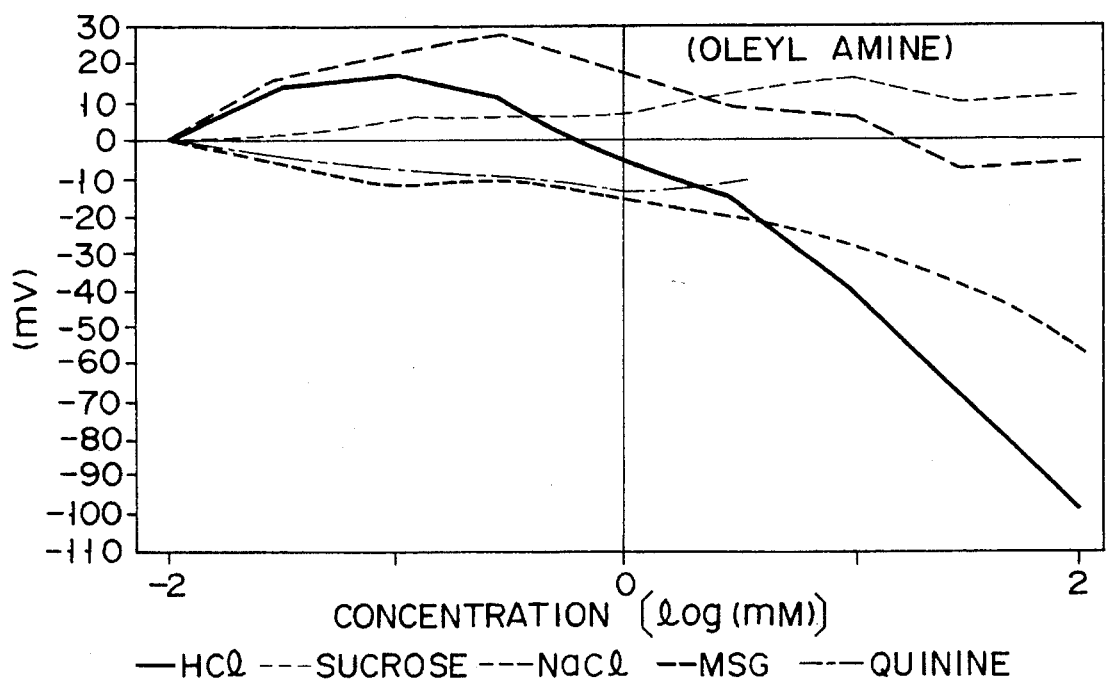
F I G. 15

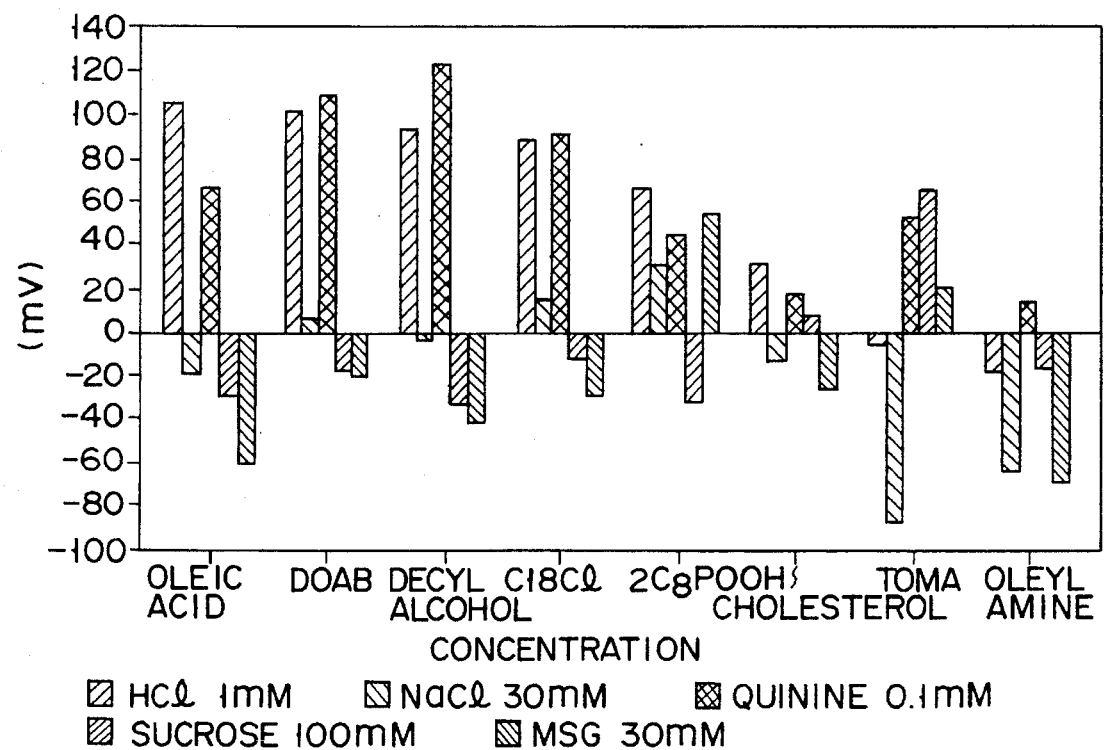
F I G. 16
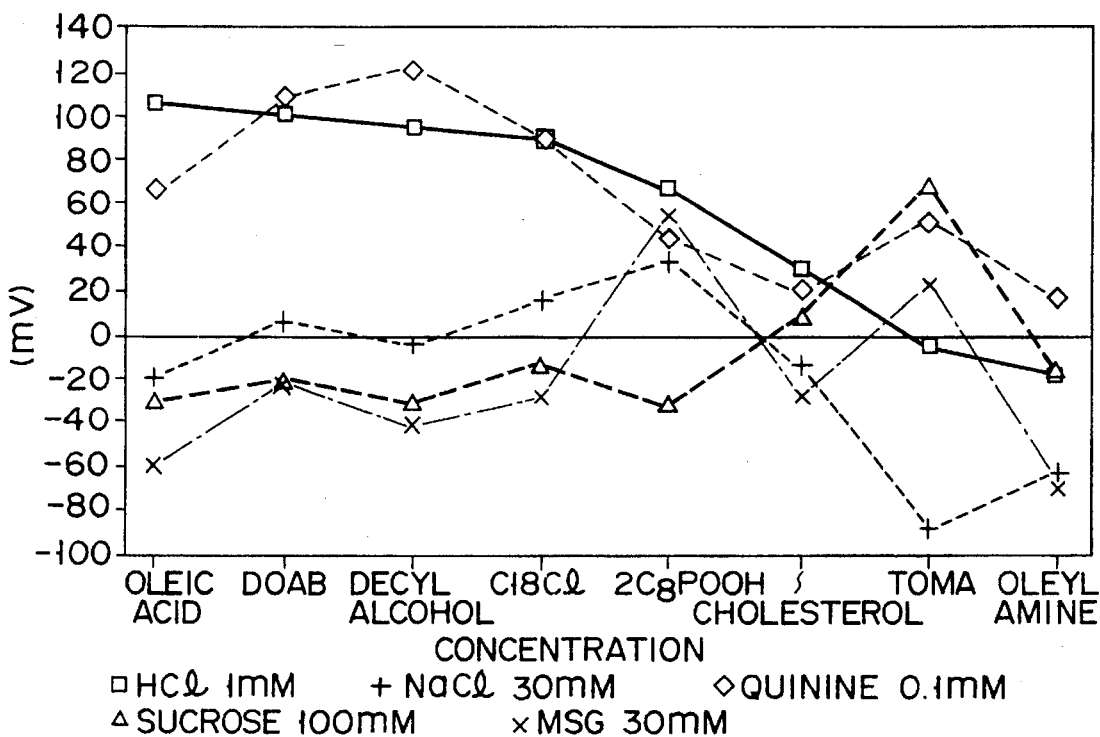
F I G. 17

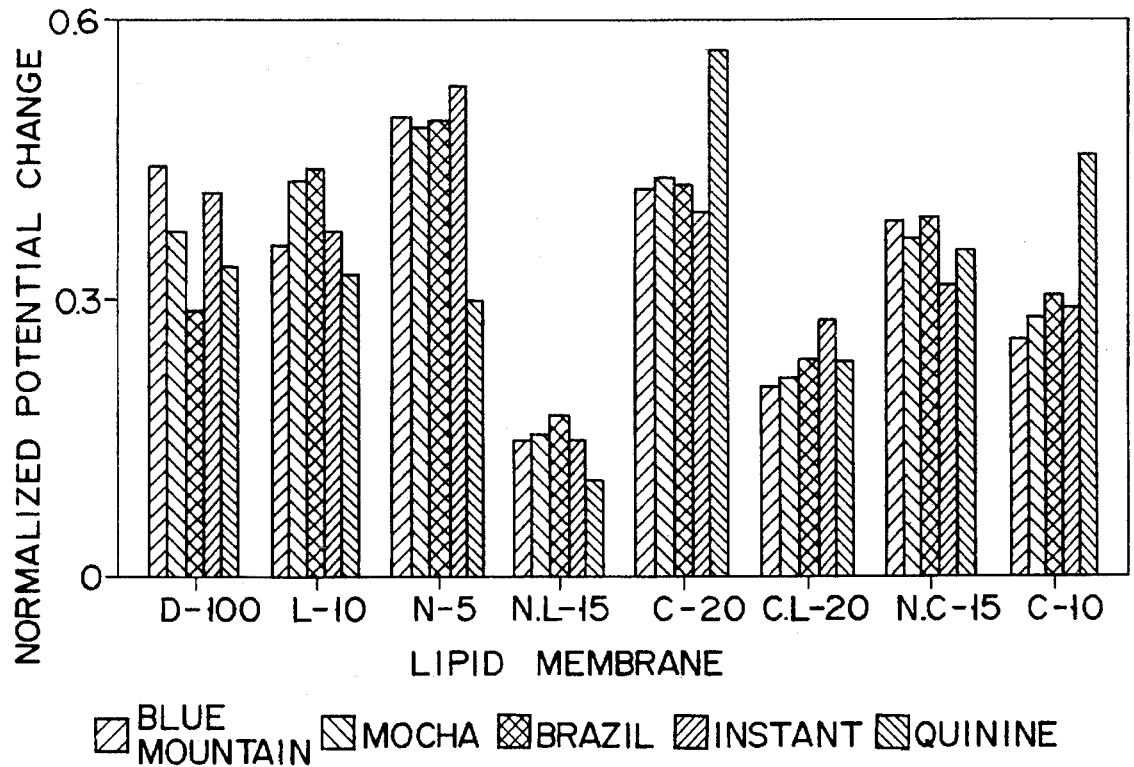
F I G. 19
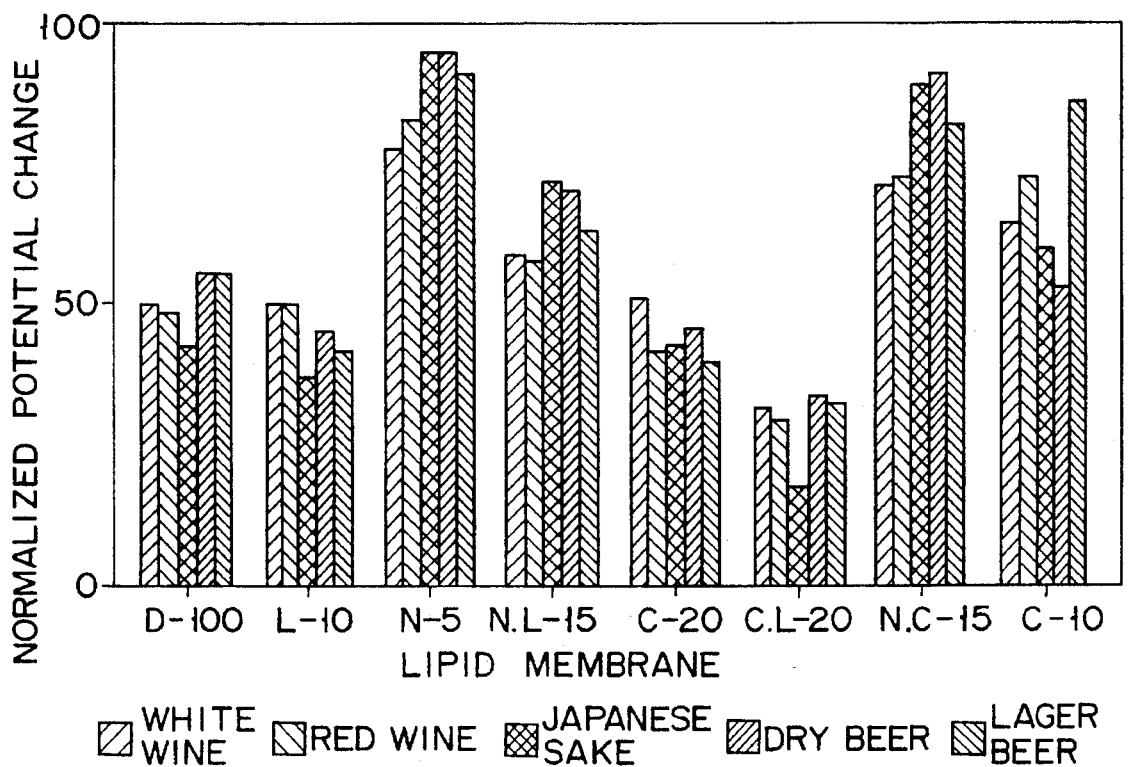
F I G. 20

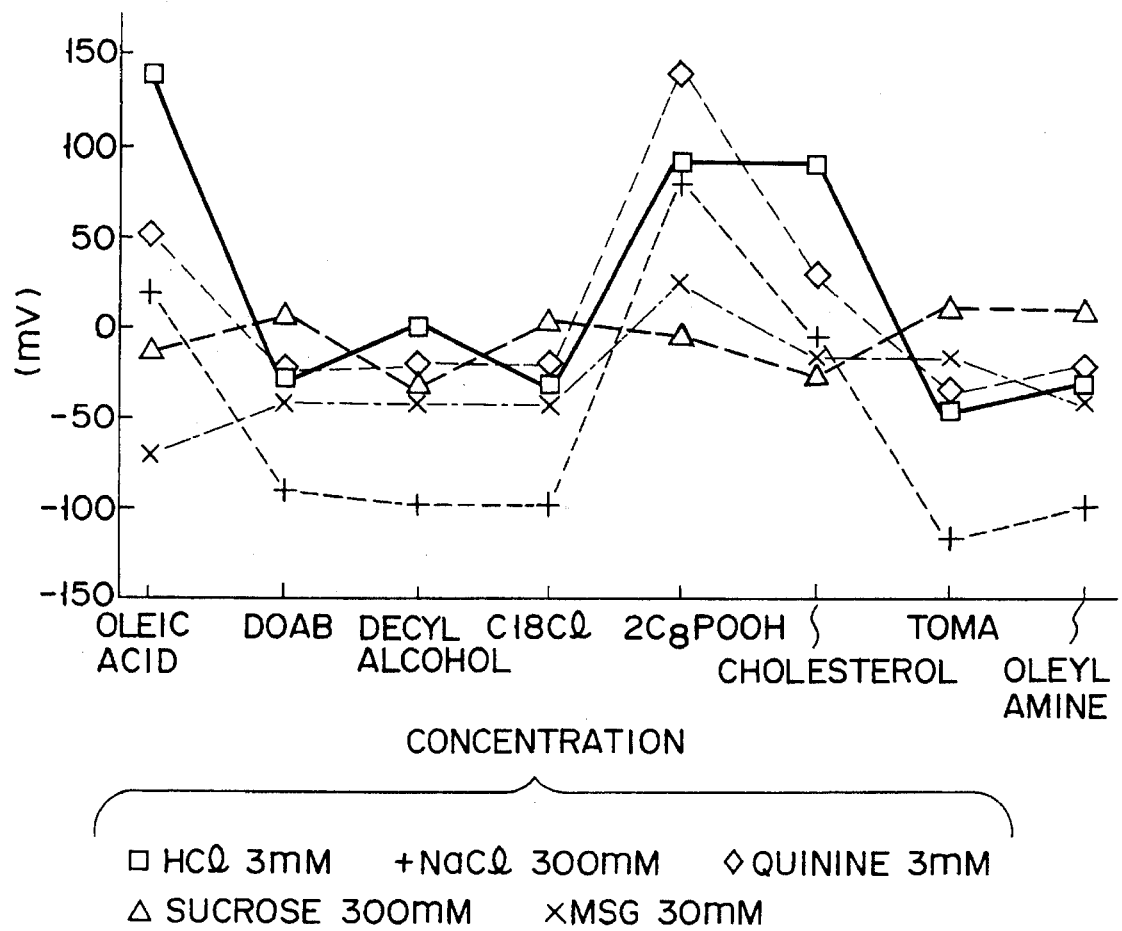
F I G. 28

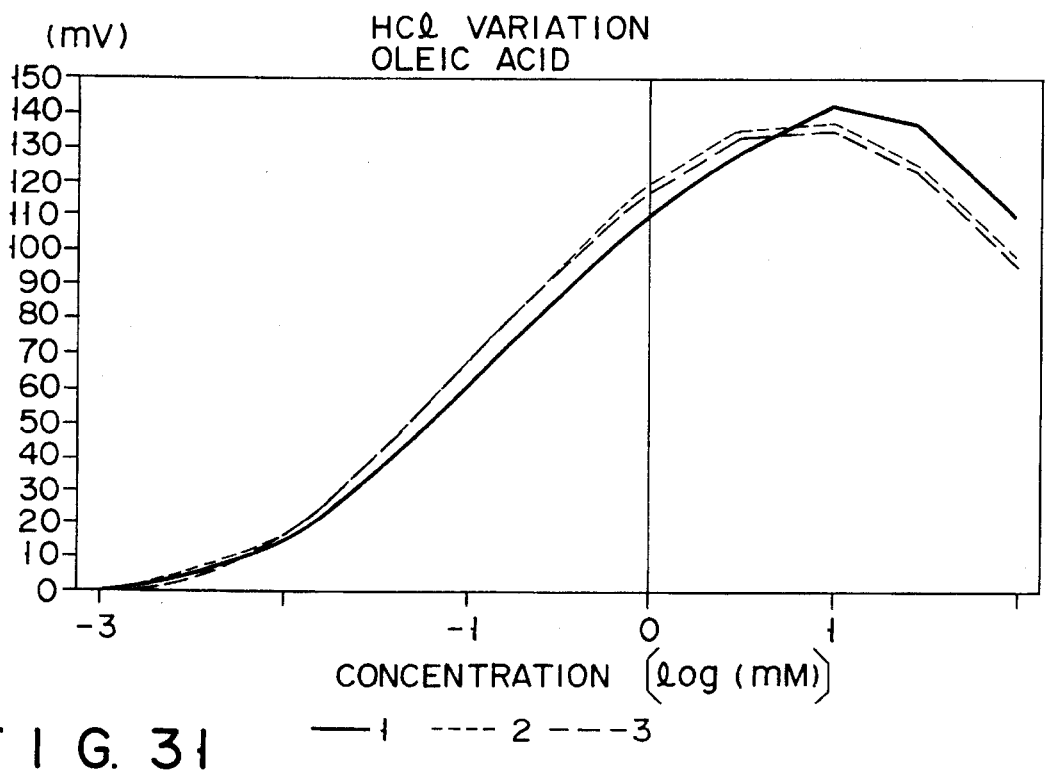
F I G. 31
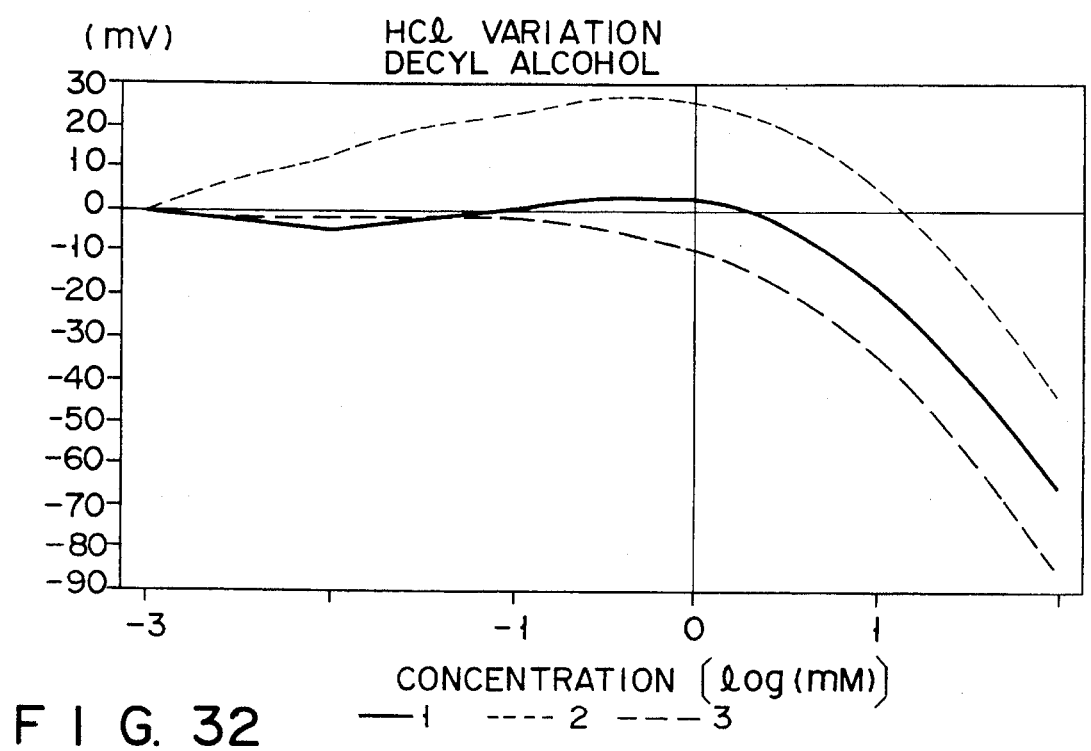
F I G. 32

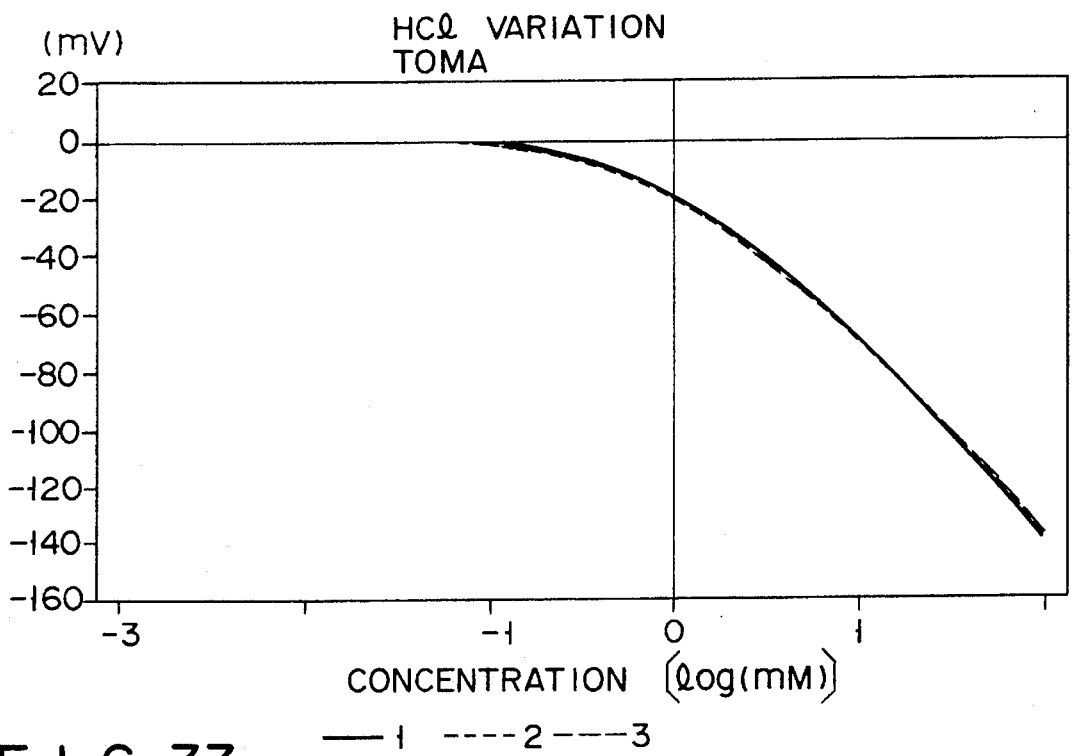
F I G. 33
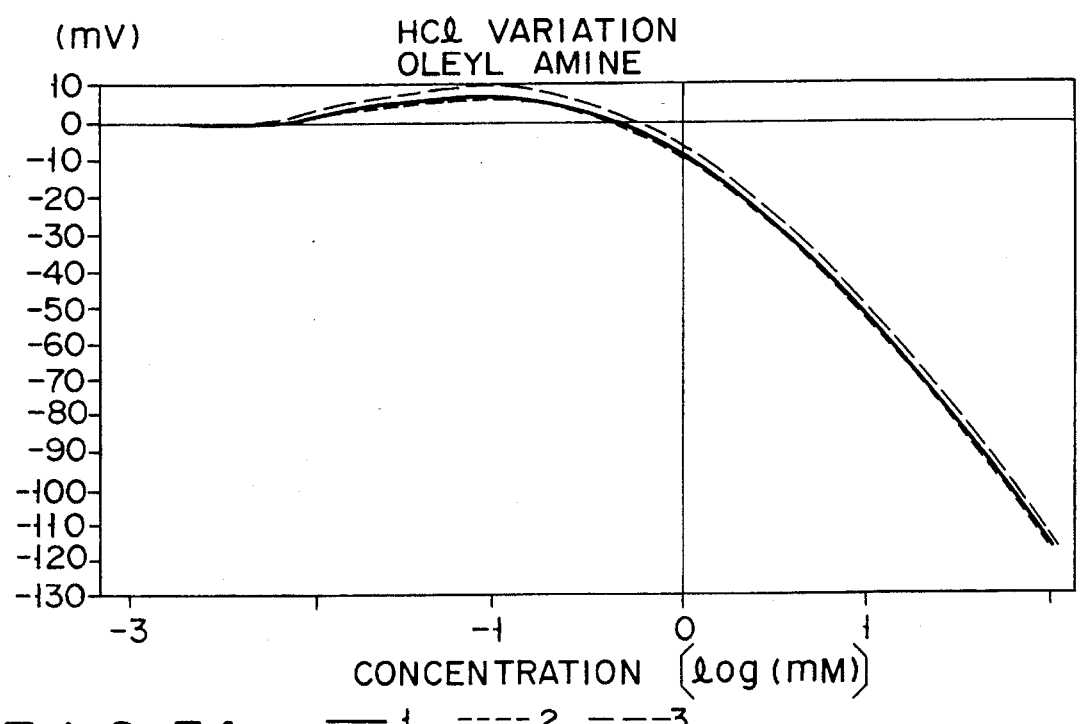
F I G. 34

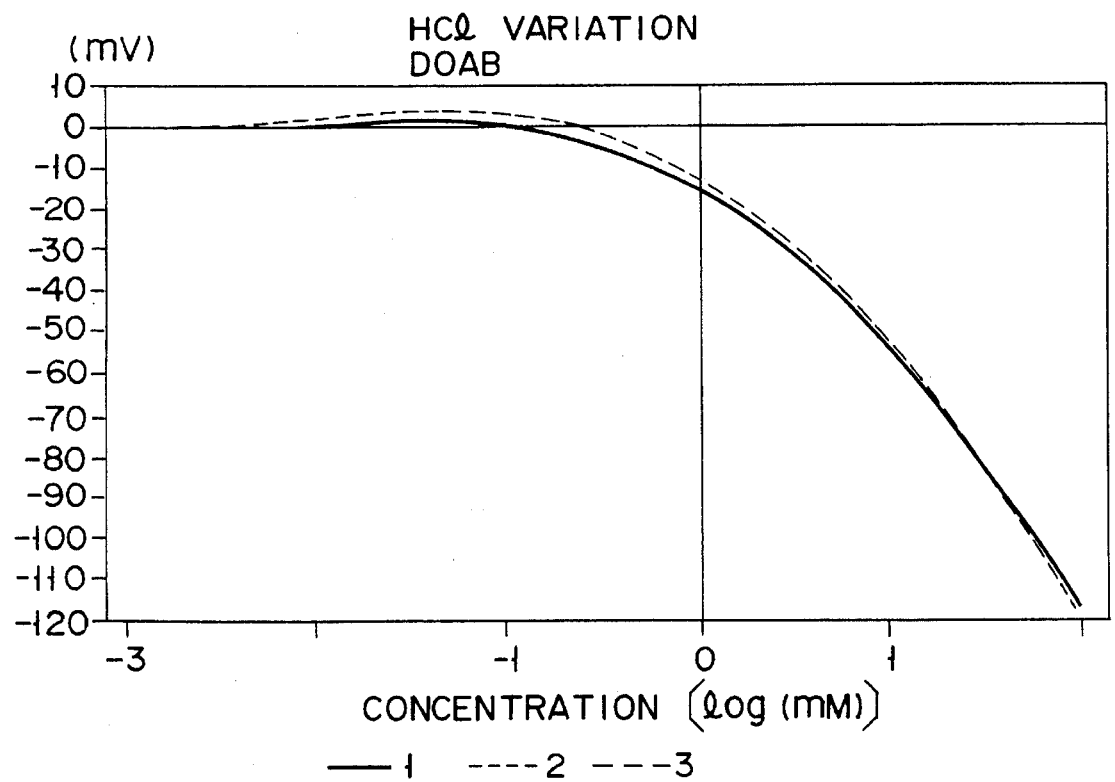
F I G. 35
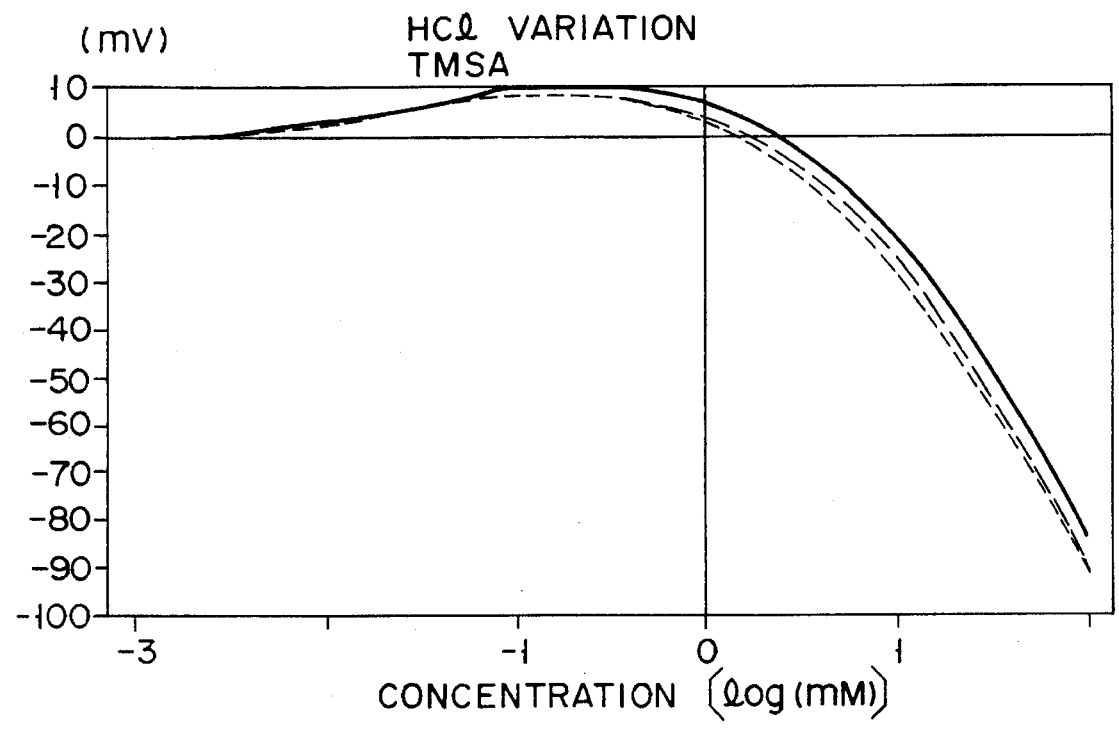
F I G. 36

TASTE SENSING SYSTEM USING ARTIFICIAL LIPID MEMBRANES

This application is a continuation of application Ser. No. 07/555,163, filed Jul. 19, 1990, abandoned.

BACKGROUND OF THE INVENTION

1. Field of the Invention

The present invention generally relates to a taste sensor and a method for manufacturing the same and, more particularly, to a taste sensor using artificial lipid membranes and a method for manufacturing the same.

The present invention relates to an artificial sensor which can replace the five senses of human and, more particularly, to a sensor or an electronic element called a transducer which can replace the sense of taste which is conventionally assumed to be the sense of human which cannot be replaced by an artificial sensor and a taste sensing system using this electronic element.

2. Description of the Related Art

Recently, as scientific techniques have progressed, various types of artificial sensors (transducers) which can perform measurement in place of the five senses of human have been developed.

For example, sensors (a term "transducer" may be more reasonable as a technical term, but a conventional term "sensor" will be used hereinafter) which sense physical amounts such as light, a sound, a temperature, and a pressure corresponding to the senses of sight, hearing, and touch are now available, and some sensors have performance superior to that of human.

Also, as a sensor for sensing a chemical amount such as the type or concentration of a chemical substance corresponding to the sense of smell or taste, an ion-sensitive field effect transistor (ISFET) or an enzyme sensor is known.

Each of these chemical sensors is considered to be characterized by its selectivity, i.e., it responds to only a specific chemical substance. However, an amount to be measured such as a smell or taste to be sensed by human may not be limited to an amount derived from a single substance but may be a combination or mixture of various types of substances. Therefore, it is assumed that realization of a sensor which can totally recognize the smell or taste leads to a sensor close to the five senses of human.

It is assumed that an amount to be measured as a combination or mixture of various types of substances is obtained via a composite effect such as a synergistic effect or a suppression effect between the substances which cause the smell or taste sensation.

Therefore, a smell or taste sensor cannot be realized by a method in which a sensor having selectivity to a specific substance is prepared for each of a plurality of types of substances and signals obtained from these sensors are simply processed by the four rules of arithmetic.

In particular, since an object to be measured by a taste sensor corresponding to the sense of taste must be an amount including a human liking, i.e., a very human factor, it is assumed that the sensor must be arranged to have a structure close to that of a living body.

A taste sensing mechanism (taste receptor mechanism) performed in a living body will be briefly described below. According to Kenzo Kurihara, "Taste", Tokyo University Publishing Society (1978), a biological membrane constituting a receptor cell receives a taste substance in response to a stimulus of the substance, and the membrane potential of the biological membrane changes accordingly. This change generates, via a synapse (a bonding portion between nerve cells called neurones), impulses which propagate in a taste nerve system. The biological membrane is a sensor for converting external information into internal information.

A taste sense organ of a vertebrate is called a taste bud which is a group of several tens of taste cells. Several taste nerves are connected to each taste cell, and a projection called a microvilli is present at the distal end of the taste cell. This projection is assumed to be a portion for receiving a substance eliciting a taste (taste substance). This microvilli membrane is a kind of a biological membrane and consists of lipids and proteins. In the biological membrane, lipids having a polarity form a membrane constituted by a polar bilayer in which hydrophobic portions oppose each other (FIG. 1), and proteins are embedded in proper amount in the polar bilayer.

Referring to FIG. 1, spherical portions indicated by circles represent hydrophilic groups a, and lines extending from the hydrophilic groups (spherical portions) represent chains b of a hydrocarbon. Two chains b extend from each hydrophilic group a in a lipid molecule shown in FIG. 1, and this expression is often used as a method of designing a chemical substance. In general, molecules called a lipid can be schematically illustrated as shown in FIG. 25. Referring to FIG. 25, a rectangle represents a rigid segment.

FIG. 2 shows a mechanism for sensing a taste. Of taste substances, sugar or amino acid which elicits sweetness is assumed to be received by an embedded protein serving as a receptor, and sourness or saltiness is assumed to be adsorbed by a hydrophilic group (whose molecular structure is schematically represented by symbols o in FIG. 2) to change the surface potential of a receptor membrane. A taste substance eliciting bitterness is assumed to be adsorbed by a hydrophobic portion (whose molecular structure is schematically indicated by thin wave forms in FIG. 2) to change the arrangement of the portion or to change an electric charge density, thereby changing the surface potential of the receptor membrane.

In the above description, saltiness, sourness, sweetness, and bitterness are exemplified as four basic tastes in accordance with a classification of physiologists. Mr. Henning uses these four tastes as polar coordinates of corners of a tetrahedron, thereby quantitatively expressing the taste (as if the taste had a shape) in the form of a tetrahedron. This expression is known as a Henning's tetrahedron (FIG. 3).

The present inventors, however, believe on the basis of the recent findings that "Umami" must be considered in addition to the above four tastes. Experimental facts concerning a conventional taste sensor will be briefly described below. According to known references, dioleyl phosphate was used as a lipid molecule, and a sample was prepared by fixing this lipid on a Millipore filter membrane known as a porous filter and used in experiments.

Dioleyl phosphate (DOPH) known as a typical lipid molecule will be described. The formula of DOPH is as follows:

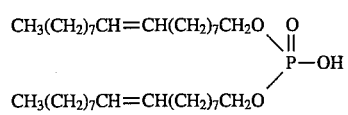

=0 and —OH groups at the right side of a phosphorus (P) atom are hydrophilic groups and negatively charged in water. Therefore, these groups attract a hydrogen ion $H^+$ and a metal ion (e.g., $Na^+$ in FIG. 2) which cause sourness and saltiness. Two carbon chains extend at the left side of the phosphorus (P) atom in correspondence with the hydrophilic groups (FIG. 2).

When the DOPH molecules are put in an aqueous solution of a salt such as potassium chloride (KCl) or sodium chloride (NaCl), the DOPH molecules are in an oil drop state (as shown at the left side of FIG. 4) if a salt concentration is low. If the salt concentration is increased, alignment gradually progresses to form a bilayer (as shown at the right side of FIG. 4) (this is a kind of phase transition).

The present inventors used a DOPH Millipore membrane prepared by adsorbing DOPH in a polymer cellulose-based support material to examine and experiment an influence of the five basic tastes on a membrane potential, a membrane resistance, and a self-excited oscillation of the membrane and reported partial results in, e.g., the following publications.

(1) MEMBRANE, 12(4), pp. 231 to 237 (1987).

(2) Proc. of the 22nd Jap. Symp. on Taste and Smell (1988), pp. 213 to 216.

(3) Agric. Biol. Chem. 50(11), pp. 2709 to 2714 (1986).

In publication (1), it is reported that the membrane potential and the membrane resistance of a DOPH Millipore membrane differently respond to each of the four basic tastes (saltiness, sourness, bitterness, and sweetness), and self-excited oscillation of the DOPH Millipore membrane independently responds to the four basic tastes.

In publication (2), it is reported that "Umami" is the fifth basic taste and monosodium L-glutamate (MSG), disodium 5'-inosinate (IMP), and disodium 5'-guanylate (GNP) are exemplified as an "Umami" substance. As a result, it is found that a response to "Umami" and a mixture of "Umami" substances synergistically act on a lipid membrane. A synergistic effect is represented by the following equation:

$$y = u + \gamma uv$$

where u: the concentration of MSG in a solution, v: the concentration of IMP or GMP to be added to MSG, y: the concentration of an MSG solution which exhibits the same taste strength as that of a solution mixture of the two substances, and $\gamma$: a constant for determining the magnitude of the synergistic effect. The constant $\gamma$ for human is assumed to be represented by the following equations:

$$\gamma = 6.42 \times 10^4 \text{ (for MSG+IMP)}$$

$$\gamma = 1.48 \times 10^5 \text{ (for MSG+GMP)}$$

The following values were obtained for the DOPH millipore membrane:

$$\gamma = 6.6 \times 10^3 \text{ (MSG+IMP)}$$

$$\gamma = 1.0 \times 10^4 \text{ (MSG+GMP)}$$

That is, it was confirmed that the synergistic effect as a human taste phenomenon could be detected by the lipid membrane.

In publication (3), a suppression effect which is a phenomenon opposite to the synergistic effect was confirmed for a mixture of a salty substance (KCl) and a bitter substance (quinine) since the membrane potential change of the DOPH millipore membrane was reduced.

As described above, according to the initial research by the present inventors, it was found that self-excited oscillation of a DOPH Millipore membrane prepared by adsorbing DOPH in a Millipore membrane having 5 μm pores responds to the taste similarly to the sense of taste of human. These facts suggest that a lipid membrane may detect not only three types of taste substances, i.e., saltiness, sourness, and bitterness but also sweetness and "Umami".

The DOPH Millipore membrane, however, has several problems to be solved to realize its industrial applications. Typical problems are as follows. (1) It is difficult to obtain reproducibility of a measurement result. (2) The membrane cannot be stably used for a long time period. (3) The number of measured quantities obtained from one type of lipid membrane is limited. (4) As a result, only information which is obtained by measurement is unsatisfactory in both quantity and quality.

SUMMARY OF THE INVENTION

It is, therefore, an object of the present invention to provide a new and improved taste sensing system using artificial lipid membranes which have excellent reproducibility and stability and can provide measurement results excellent in both quality and quantity.

It is another object of the present invention to provide a taste sensor using lipid membranes which have excellent reproducibility and stability.

It is still another object of the present invention to provide a method for manufacturing a taste sensor using lipid membranes which have excellent reproducibility and stability.

More specifically, it is an object of the present invention to realize a taste sensor as a taste sensing system for sensing the taste which is concerned with the sense of taste, a very human liking. This taste sensor aims at achieving the following several subjects.

(a) The taste sensor must have a function of sensing a taste with one of the five senses of human as close as possible.

(b) An output from the taste sensor must be an electric signal (a current, a voltage, a transient phenomenon, or self-excited oscillation).

(c) An output from the taste sensor must be stably obtained, and data having reproducibility must be obtained.

(d) The taste sensor must have a structure which can be easily brought into contact with a food as an object to be examined.

(e) Since a living body has metabolism, sense organs of a living body can be repetitively used as long as the body lives. Similarly, the taste sensor must withstand repetitive use for a long time period.

(f) The taste sensor must sense "Umami" in addition to the four basic tastes, saltiness, sourness, sweetness, and bitterness.

(g) The taste sensor does not perform simple addition of outputs concerning the basic tastes but must detect a mixing effect such as a synergistic effect or a suppression effect of the basic tastes.

According to the present invention, in order to achieve the subjects enumerated above and therefore the objects of the present invention, substantially the following methods are adopted to realize a taste sensor similar to a living body, human as close as possible.

(A) A membrane including a material called a lipid is formed, and electric characteristics (e.g., a membrane potential, a conductivity, a transient phenomenon, and an amplitude or frequency of self-excited oscillation) of the membrane are detected.

[corresponding subjects: (a), (b), and (g)]

(B) The lipid membrane is formed by mixing a polymer material having a matrix structure on its surface.

[corresponding subjects: (a), (c), (d), and (e)]

(C) Lipid molecules are composed of a hydrophobic portion consisting of elongated molecules and a hydrophilic portion at one end of the elongated molecules. The lipid molecules are arranged such that at least some of the hydrophilic groups are exposed on the surface in the surface matrix of the polymer material.

[corresponding subjects: (a), (c), and (e)]

(D) An electrode is connected to be in contact with the hydrophobic group side of the lipid molecules. It is sometimes preferred to place a special buffer member at a contact portion between the electrode and the membrane containing the lipid molecules.

[corresponding subjects: (a), (b), (c), and (d)]

(E) An arrangement is made such that a response to the basic tastes (including umami) can be changed by changing the type and composition ratio of the lipid molecules. Some examples will be described later.

Also, a plurality of types of lipid molecules are used to obtain multi channels of electric signals to be detected, thereby enabling a correlation arithmetic operation, decision-by-majority processing, synergistic effect processing, suppression effect processing, and the like between the signals.

[corresponding subjects: (a), (b), (f), and (g)]

(F) An aqueous solution of an electrolyte is used to define an orientation of the lipid molecules in the matrix, so as to increase the sensitivity of the taste sensor.

[corresponding subjects: (c) and (e)]

(G) An aqueous solution of a salt is used to reproduce or reserve the lipid membrane.

[corresponding subjects: (c) and (e)]

(H) As a lipid, a molecule consisting of a saturated hydrocarbon group having a hydrophilic portion, such as a phosphoric acid group, an amino group, an ammonium group, a carboxyl group, or a hydroxyl group is adopted.

[corresponding subjects: (a), (c), and (g)]

According to a first aspect of the present invention, there is provided a taste sensing system comprising:

a taste sensor, having a lipid membrane comprising lipid molecules and a membrane-forming material for accommodating at least some of the lipid molecules on its surface, for inducing a change in electrical characteristics when taste substances interact with the surface of the lipid membrane; and signal processing means for receiving a signal indicating the change in electrical characteristics induced by the taste sensor to generate data for determining the tastes of the taste substances.

According to a second aspect of the present invention, there is provided a taste sensor comprising:

a lipid membrane for reacting with taste substances to induce a change in electrical characteristics, the lipid membrane including a) lipid molecules having a hydrophobic portion in which an atomic array extends in the longitudinal direction and a hydrophilic portion present at a portion of the atomic array extending in the longitudinal direction; and b) a membrane-forming material having a matrix structure for receiving the lipid molecules on its surface, wherein at least some of the lipid molecules are accommodated in the matrix structure of the membrane-forming material such that the hydrophilic portion is arranged on the surface, and the lipid membrane induces a change in electrical characteristics in accordance with a change in electrical characteristics of the hydrophilic portion arranged on the surface, when the taste substances react to the lipid molecules arranged at least essentially on the surface of the lipid membrane.

According to a third aspect of the present invention, there is provided a method of manufacturing a taste sensor, comprising the steps of:

preparing a base material to thereby mix a lipid material having a hydrophobic portion in which an atomic array extends in the longitudinal direction and a hydrophilic portion present at a portion of the atomic array extending in the longitudinal direction, a membrane-forming material formed into a membrane-like solid having a matrix structure on its surface, and a plasticizer required by the membrane-forming material at a predetermined mixing ratio;

forming a shallow and wide liquid surface to thereby add a solvent of the membrane-forming material to the base material having the predetermined mixing ratio, so as to dissolve the base material and obtain an essentially homogeneous mixture, and volatilizing the solvent from the shallow and wide liquid surface to form a lipid membrane.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 3 is a schematic view showing a Henning's tetrahedron for explaining the related art;

FIG. 4 is a schematic view showing phase transition of DOPH for explaining the related art;

FIG. 5 is a schematic sectional view showing a taste sensor according to an embodiment of the present invention;

FIGS. 8 to 15 are graphs showing potential responses of various types of lipid membranes with respect to basic taste substances obtained by the measuring circuit shown in FIG. 7A;

FIGS. 16 and 17 are graphs each showing basic taste response characteristics expressing the potential response characteristics of the various lipid membranes shown in FIGS. 8 to 15 in another view;

FIG. 19 is a graph showing membrane potential response patterns obtained by the taste sensor of the present invention with respect to various types of coffees;

FIG. 20 is a graph showing membrane potential response patterns obtained by the taste sensor of the present invention with respect to various types of liquors;

FIGS. 27(A) to 27(H) and FIG. 28 are graphs showing potential responses of an 8-channel taste sensor array of the present invention with respect to five basic taste substances in different aspects; and FIGS. 29 to 36 are graphs showing variations in potential response with respect to HCl obtained by the respective lipid membranes for estimating the reproducibility of the taste sensor of the present invention.

DETAILED DESCRIPTION OF THE PREFERRED EMBODIMENTS

Figure 1:
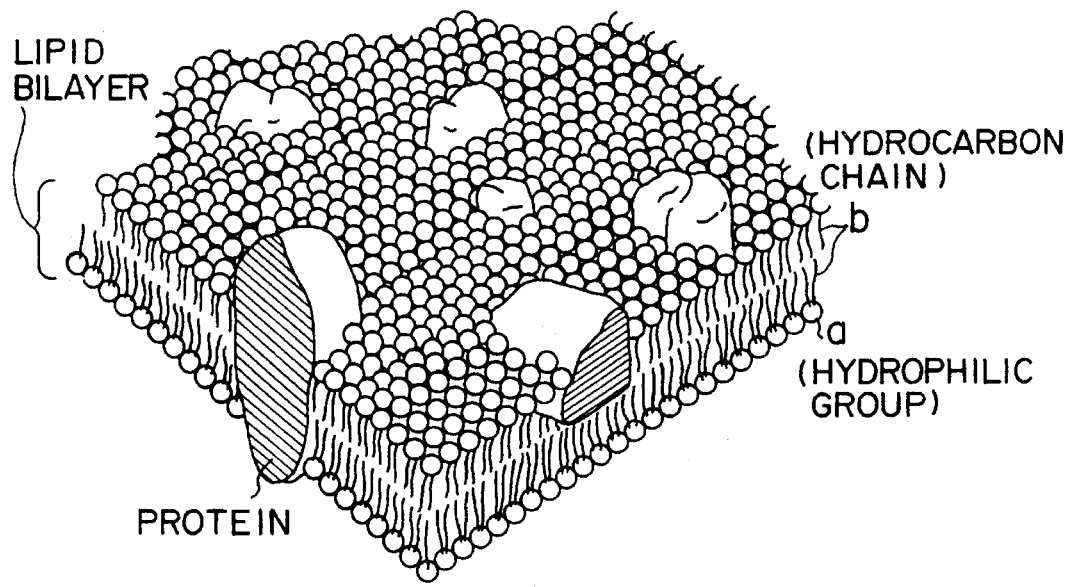
FIGS. 1 and 2 are schematic views showing a microvilli membrane for explaining the related art.

Reference will now be made in detail to the presently preferred embodiments of the invention as illustrated in the accompanying drawings, in which like reference characters designate like or corresponding parts throughout the several drawings.

[ Lipid Membrane ]

Examples of lipid substances as a basic material for forming a lipid membrane for use in a taste sensor of the present invention are summarized in Table 1. Table 1 shows 11 types of lipid molecules.

These lipid substances were received singly or as a mixture of two or more thereof in a membrane-forming material to form a lipid membrane, thereby realizing a taste sensor.

Figure 2:
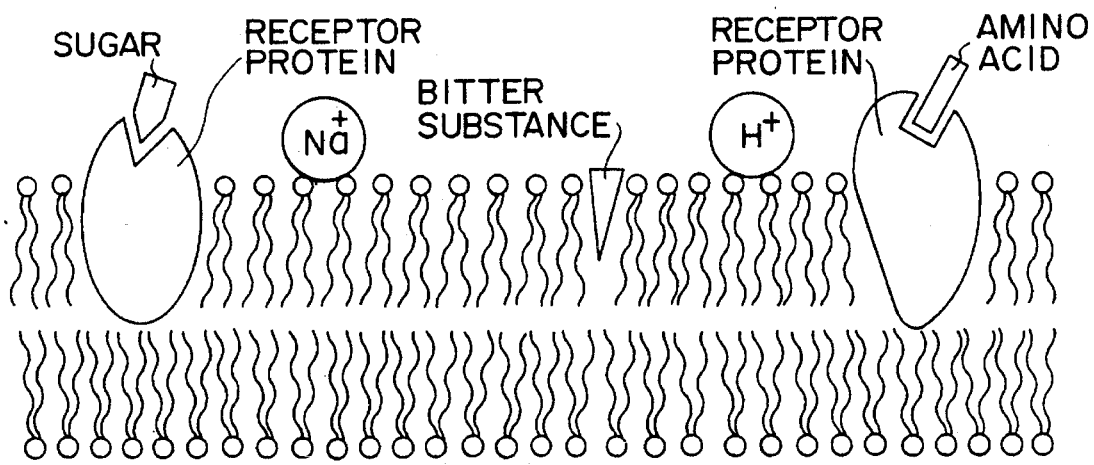

As schematically shown in FIGS. 1 and 2, the molecular structure of these lipid substances is characterized by comprising a hydrophobic portion in which an atomic array extends in the longitudinal direction and a hydrophilic portion present at or near one end of the atomic array. In addition, a phosphoric acid group, an amino group, a carboxyl group, a hydroxyl group, and the like are present as the hydrophilic portion. In Table 1, main functional groups in a biological membrane of a living body are listed up as a lipid.

TABLE 1

| No. | Name (Abbreviation) |
|---|---|
| 1. | dioctylphosphate ($2C_8POOH$) |
| 2. | cholesterol |
| 3. | trioctylmethyl ammonium chloride (TOMA) |
| 4. | oleic acid |
| 5. | n-octadecylchloride |
| 6. | diphenyl phosphate |
| 7. | decylalcohol |
| 8. | dioctadecyldimethylammonium bromide (DOAB) |
| 9. | lecithin |
| 10. | trimethyl stearyl ammoniumchloride (TMSA) |
| 11. | oleylamine |

In samples in which the lipids listed in Table 1 were mixed at several mixing ratios, a component α was added to dioctylphosphate as a phospholipid to form lipids as listed in Table 2. Abbreviations of these samples are listed in the rightmost column in Table 2.

TABLE 2

| | Mixture with Phospholipid ($2C_8POOH + α$) | |
|---|---|---|
| No. | Mixture | Abbreviation |
| (1) | $2C_8POOH$ 100 wt % | D-100 |
| (2) | $2C_8POOH$ + DOAB 5 wt % | N-5 |
| (3) | $2C_8POOH$ + cholesterol 10 wt % | C-10 |
| (4) | $2C_8POOH$ + cholesterol 20 wt % | C-20 |
| (5) | $2C_8POOH$ + lecithin 10 wt% | L-10 |
| (6) | $2C_8POOH$ + DOAB 5 wt % + cholesterol wt % | N.C-15 |
| (7) | $2C_8POOH$ + DOAB 5 wt % + lecithin 10 wt % | N.L-15 |
| (8) | $2C_8POOH$ + cholesterol 10 wt % + lecithin 10 wt % | C.L-20 |

Figure 26A:
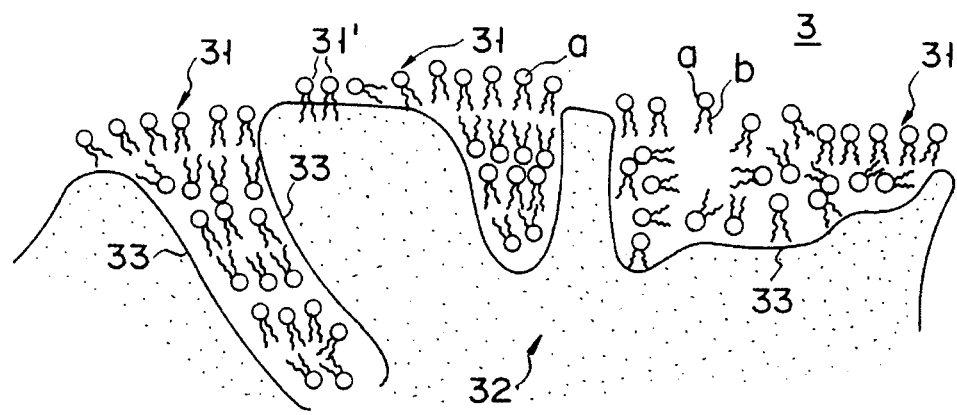
FIG. 26A is a schematic view showing a structure of a lipid membrane for use in the taste sensor of the present invention.

FIG. 26A shows a schematic view of formation of a lipid membrane 3 for use in the present invention by an expression method used in a designing method of a chemical substance. Each lipid molecule shown in FIG. 26A includes a hydrophilic group a, e.g., a hydrophilic portion a represented by a spherical portion which is indicated by a circle, and a chain structure b (e.g., an alkyl group) of a hydrocarbon in which an atomic array extends. In FIG. 26A, two chains extend to represent one molecule, thereby constituting molecules as a whole. This chain portion of the hydrocarbon is a hydrophobic b̲. These molecules 31 are received in a surface structure of a matrix 33 of a membrane material 32, i.e., in the surface of a planar wide micro structure and inside the matrix 33 so that they are dissolved therein (e.g., 31' in FIG. 26A). The molecules 31 are accommodated such that the hydrophilic portions are arranged on the surface. This manner becomes similar to that as shown in FIGS. 1 and 2.

Forming of the lipid membrane as shown in FIG. 26A will be described below.

In order to form a lipid membrane, a matrix for supporting a lipid must be prepared. Therefore, thermoplastic polyvinyl chloride [$CH_2CHCl$]n (PVC) which can be easily obtained and processed was used as the matrix. Since PVC can be dissolved in tetrahydrofuran (THF), nitrobenzene, cyclohexanone, and the like and made either soft or hard by changing a mixing ratio with respect to a plasticizer, it can be flexibly used in accordance with its application. In addition, PVC is stable in quality and can be easily molded.

Figure 26B:
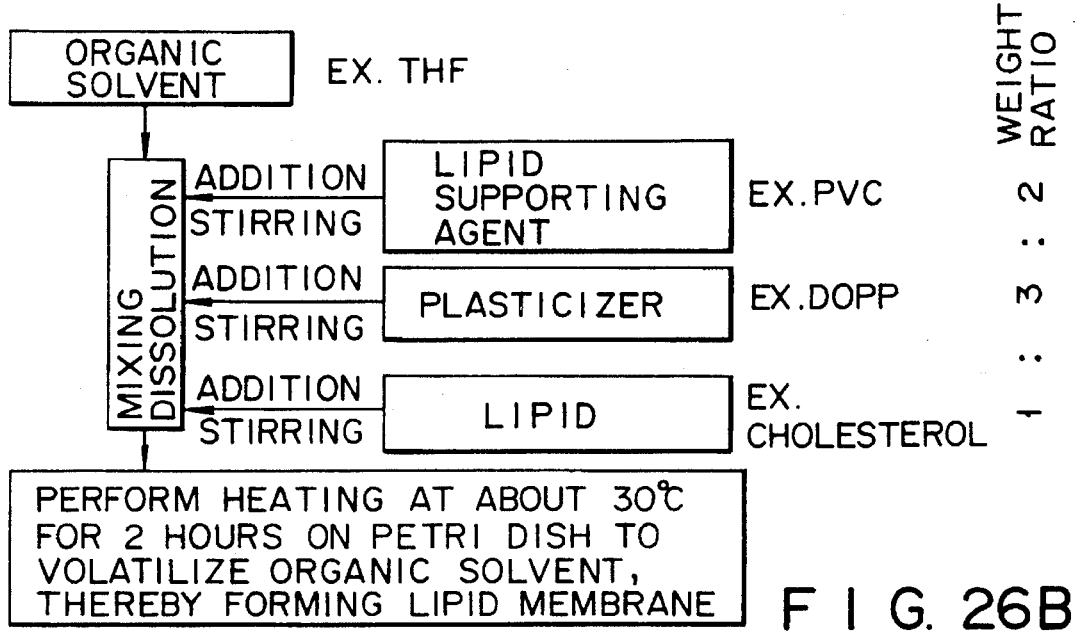
FIG. 26B is a view showing formation steps of the lipid membrane for use in the taste sensor of the present invention.

PVC as the matrix base material, a plasticizer, and a lipid are mixed at a weight ratio of about 2:3:1. If no plasticizer is added, a prepared lipid membrane undesirably becomes cloudy or nonhomogeneous. A prepared lipid membrane may also become cloudy or nonhomogeneous in accordance with the type of selected lipid or plasticizer, a mixing ratio, or a mixing method. As a plasticizer, dioctyl phthalate (DOP), dioctylphenylphosphonate (DOPP), or tricresyl phosphate (TCP) was used. If the same lipid is prepared, response characteristics for a taste slightly differ, according to the types of the mixed plasticizer. About 400 mg of a mixture including the plasticizer, each of the lipids (or a mixture thereof) listed in Tables 1 and 2, and PVC were dissolved in 10 cc of THF as an organic solvent, and the resultant mixture was put in a vessel with a flat bottom (e.g., a petri dish having a diameter of 85 mm). The mixture was held at about 30° C. for about two hours on a uniformly heated base plate to volatilize THF, thereby forming a substantially transparent and colorless lipid membrane. FIG. 26B shows lipid membrane formation steps. The thickness of the lipid membrane prepared in this manner was about 200 μm.

Although THF can be volatilized under a reduced pressure at room temperature, a better lipid membrane can be obtained when the material is heated more or less.

In such a lipid membrane, it is assumed that the lipid and the plasticizer are fixed in a texture of the surface matrix of a plastic material, PVC. When this lipid membrane is dipped in salt water or an electrolyte solution such as an aqueous potassium chloride solution having a concentration of about 10 m mole/l for about one minute, a molecular array in which the hydrophilic groups of the lipid are arranged on the surface is stably obtained, thereby realizing a practically more preferable function as a taste sensor. The above electrolyte solution is suitable for preserving a lipid membrane for a taste sensor. That is, while a lipid membrane left to stand in air was degraded on the order of days, no degradation was found in a lipid membrane dipped in this solution on the order of years.

It was also confirmed that the solution had a function of reproducing a lipid membrane which was degraded after being left to stand in air.

Note that substances listed in Table 3 were used in place of PVC as a base material for forming a matrix for fixing a lipid. As a result, similar electrical characteristics as a taste sensor were obtained.

When a lipid membrane prepared in this manner was dipped in an aqueous solution of potassium chloride or sodium chloride with about 10 m mole/l comprising ions as described above, at least some of the hydrophilic groups of the lipid molecules fixed in the matrix such as PVC were aligned on the surface (toward the aqueous solution). That is, functions and sensitivities as a taste sensor were improved.

TABLE 3

| Polymer Material as Base of Lipid Membrane | |
|---|---|
| polystyrene | celluloseacetate |
| polysulfone | cellulosetriacetate |
| polycarbonate | celluloseacetatebutylate |
| polyallylate | agar |
| polyethylsulfone | k-caraginane |
| polysulfone sulfonate | sodium arginate |
| aromatic polyamide | epoxy |
| polyglutamate | poly p xylylene |
| polyvinylchloride | Teflon (registered trademark) |
| polyvinylalcohol | Japanese lacquer |
| polyacrylonitrile | |
| polyvinyldifloride | |

TABLE 3-continued

| Polymer Material as Base of Lipid Membrane |
|---|
| polyester urethane |
| polyvinylbutyral |
| polyvinylpyridine |
| NYLON 66 (tradename) |

[Taste Sensor, Electrode]

Various types of lipid membranes prepared as described above (each cut into a square member having about 3-mm side) were used to constitute taste sensors for actual measurements. FIG. 5 is a schematic view (sectional view) showing an electrode for the taste sensors manufactured for actual measurements. An insulating base plate 1 is, e.g., an acrylic resin plate having a thickness of 2 mm, and an electrode 2 is attached thereto.

Referring to FIG. 5, a hole having a diameter of 0.5 to 1.5 mm was formed in the base plate 1, and a silver rod having a corresponding diameter was inserted therein as the electrode 2. Although gold or platinum can be used as the electrode 2, these materials are expensive. When silver or copper is used as the electrode 2, a non-polarized molecular layer or a molecular layer which can be ionized is preferably formed as a buffer layer 4 at a contact portion with respect to a lipid membrane 3 in accordance with an application (depending on whether self-excited oscillation is to be observed or a membrane potential or conductivity is to be measured). The electrode 2 and a lead wire of the electrode 2 may be used circuits printed on the flat surface of the base plate 1.

In order to mount the lipid membrane 3 on the base plate 1, the lipid membrane 3 was adhered to be in contact with the electrode 2 via the buffer layer 4 and then adhered on an acrylic plate as the base plate 1 by using THF in which 10% of PVC was dissolved. Thereafter, THF was volatilized to form a structure as shown in FIG. 5.

Figures 6A, 6B:
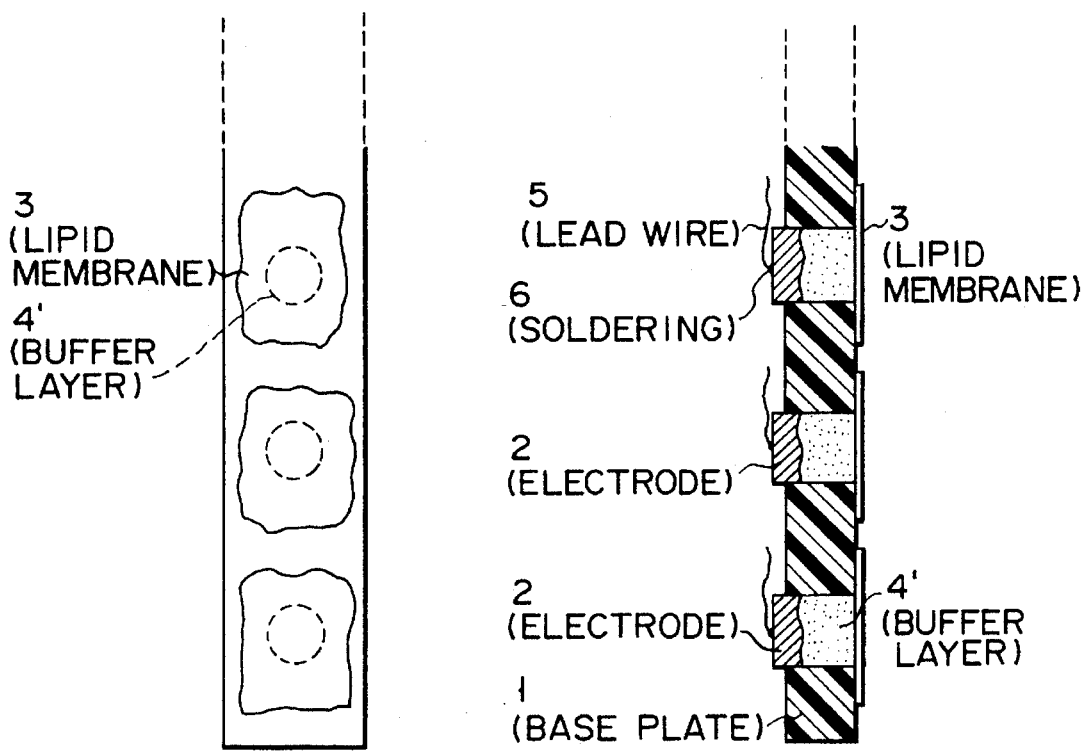
FIGS. 6A and 6B are schematic front and sectional views, respectively, showing a taste sensor according to another embodiment of the present invention.

FIGS. 6A and 6B show another taste sensor for actual measurement. FIG. 6A is a front view showing three sensing parts of multi-channel array sensors. Each of FIGS. 5 and 6A shows only parts of array sensors. In an actual structure, however, a plurality of various types of lipid membranes having different response characteristics must be arranged in parallel with each other to increase the number of signals extracted from a taste sensor, thereby obtaining a satisfactory amount of signals as taste information for reproducing the sense of taste of human from the taste sensor.

FIG. 6B is a sectional view of the taste sensor. Referring to FIG. 6B, the structure of an electrode 2 is slightly different from the electrode structure shown in FIG. 5. Firstly, a lead wire 5 is additionally soldered to the electrode 2. Secondly, as a buffer layer 4', a layer prepared by adding potassium chloride (KCl) having a concentration of 100 m mole/l (mM) to agar-agar was used. This buffer layer maintains a Cl$^-$ concentration around silver chloride constant and therefore is equivalent to the electrode system shown in FIG. 5 as an electrode for measuring a conductivity of a lipid membrane. In addition, since a salt concentration gradient can be given to a membrane, the membrane can be set in a state closer to a living system. This buffer layer suppresses a potential change between the electrode and membrane invited by reacting ions in a solution to be measured to the electrode as a metal.

[Measuring System]

Figure 7B:
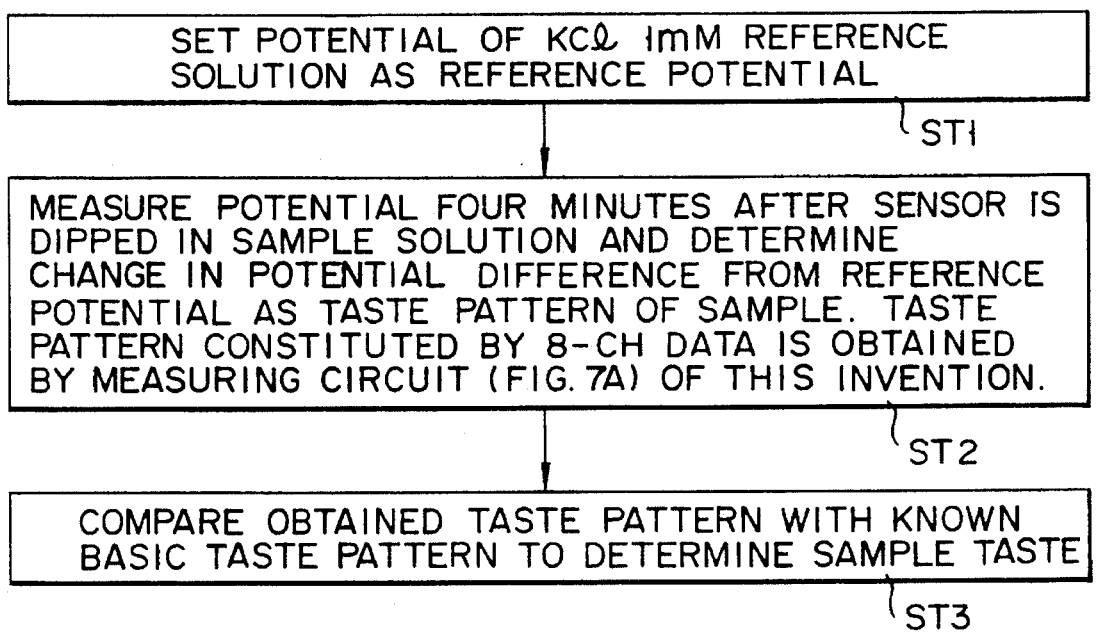
FIG. 7B is a flow chart for explaining signal processing of a micro computer shown in FIG. 7A.
Figure 7A:
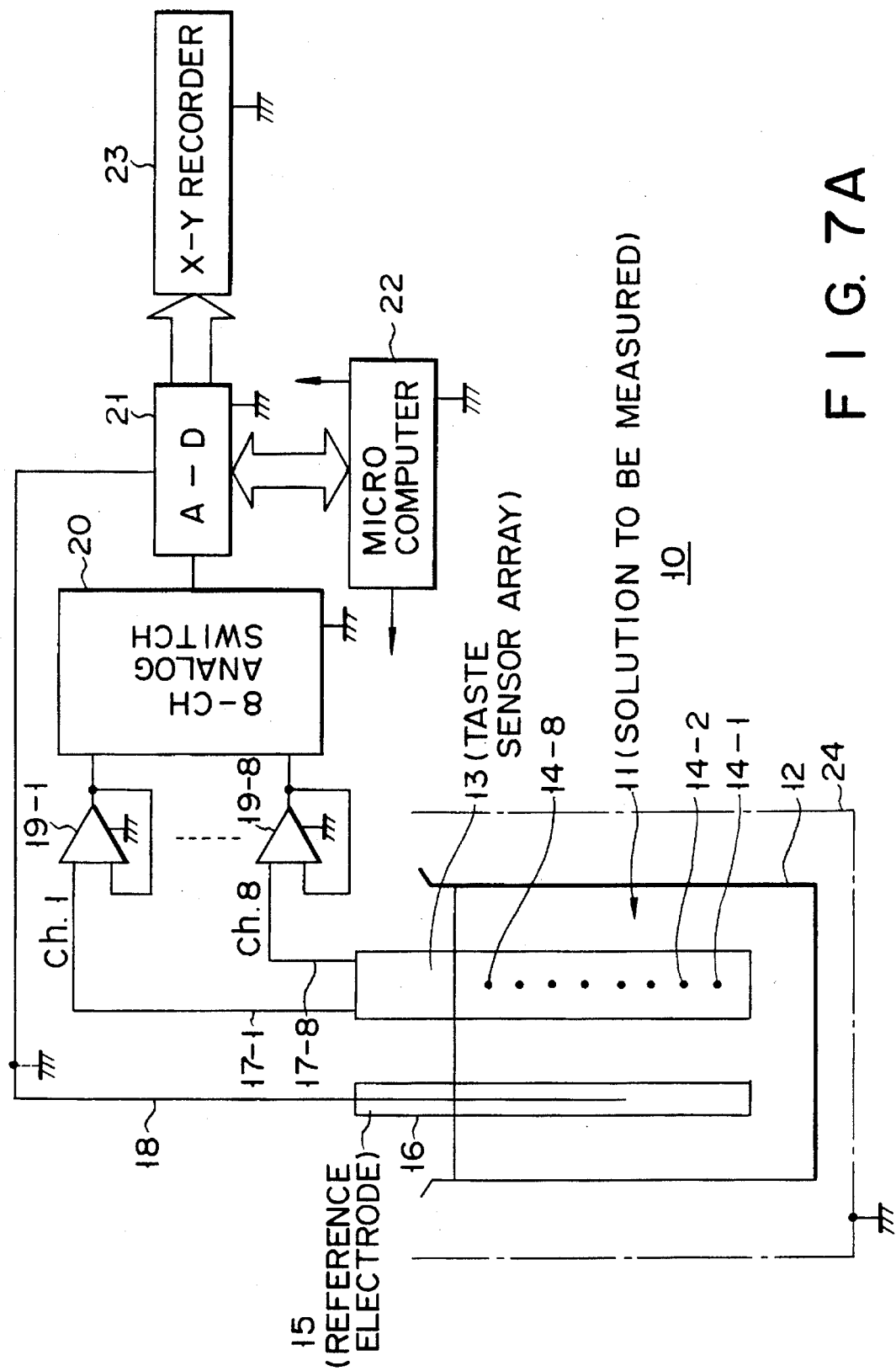
FIG. 7A is a block diagram showing a membrane potential measuring circuit of the taste sensor of the present invention.
Figure 8:
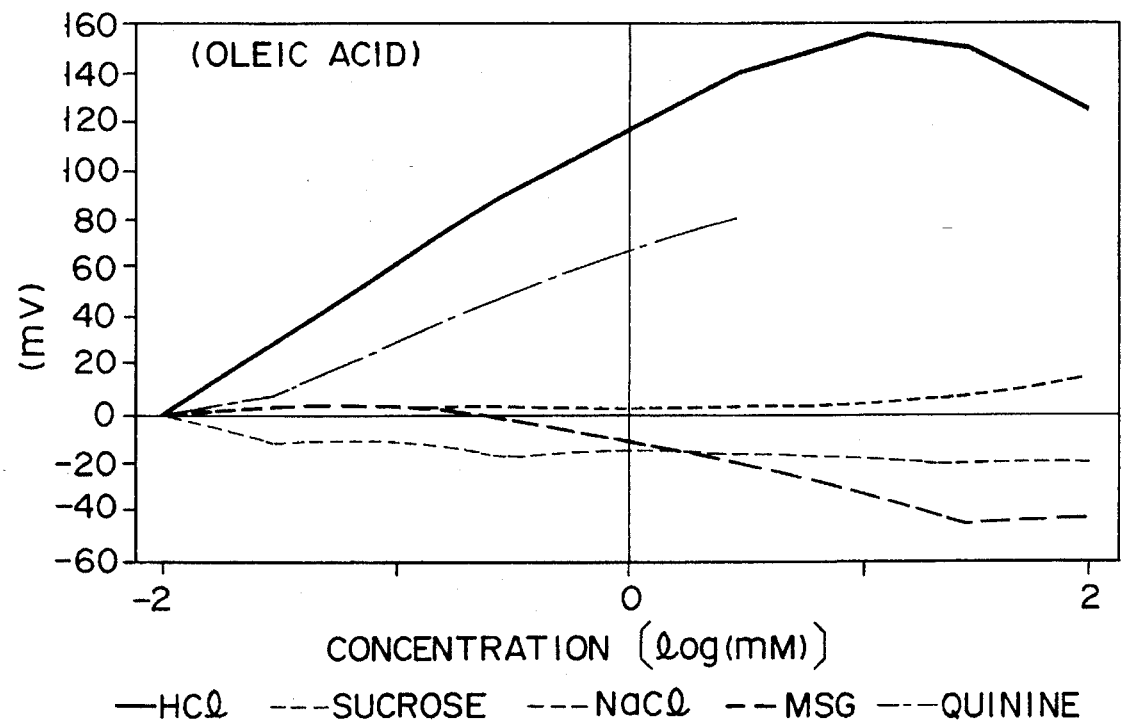
Figure 9:
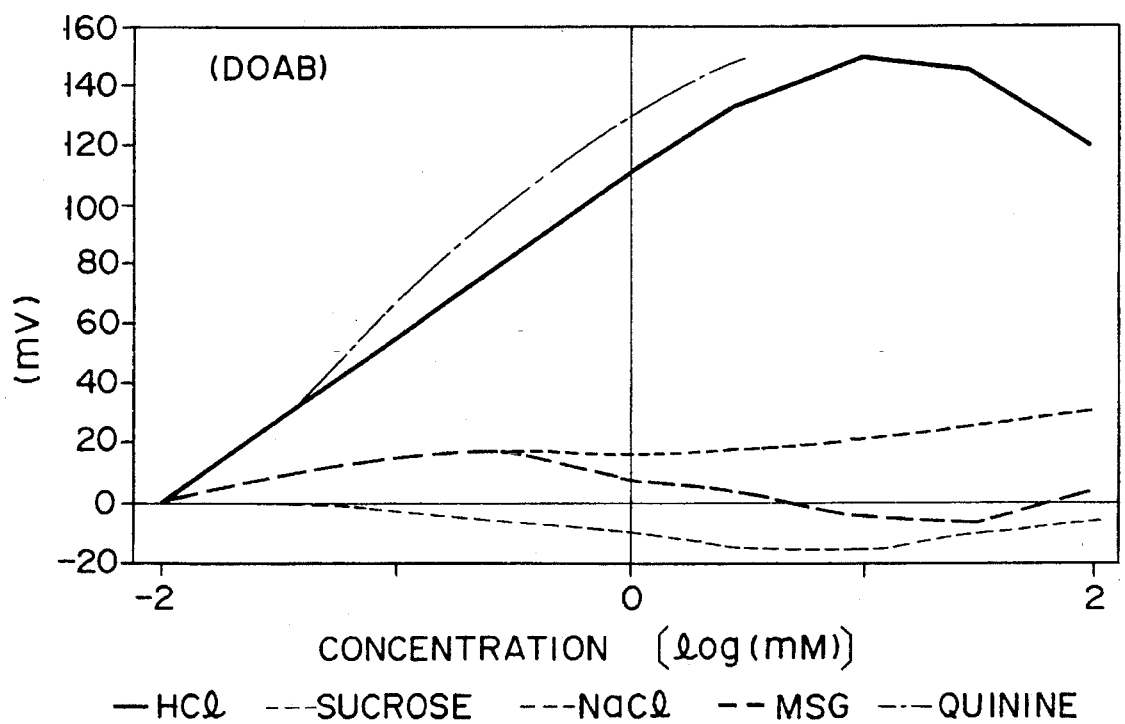

FIG. 7A shows a basic arrangement 10 of a measuring system for extracting signals from a taste sensor. An aqueous solution of taste substances was prepared and put as a solution 11 to be measured in a vessel 12 such as a beaker. As the taste substances, sodium chloride (NaCl) eliciting saltiness, hydrogen chloride (HCl) eliciting sourness, quinine hydrochloride eliciting bitterness, and sucrose eliciting sweetness as the four basic tastes, and monosodium glutamate (MSG) eliciting "Umami" were used. Also, coffees and liquors were added as substances to be measured (to be described later). A taste sensor array 13 manufactured by arranging a plurality of lipid membranes 3 and electrodes 2 on an acrylic base plate 1 as described above was put in each solution to be measured. Before the sensor array was used, an electrode potential was stabilized by using an aqueous solution of potassium chloride having a concentration of 10 m mole/l. In FIG. 7A, black dots 14-1, . . . , 14-8 represent the lipid membranes.

A reference electrode 15 was prepared as an electrode for generating a reference potential of measurement and put in the solution to be measured. The taste sensor array 13 and the reference electrode 15 were separated from each other by a predetermined distance. The surface of the electrode 15 was covered with a material prepared by fixing potassium chloride having a concentration of 100 m mole/l in agar-agar as a buffer layer 16. Therefore, the electrode system is constituted by silver (electrode 2)|silver chloride (buffer layer 4)|lipid membrane 3 (14)|solution to be measured 11|buffer layer (potassium chloride 100 m mole/l) 16|silver chloride (buffer layer 4)|silver (electrode 2).

Electrical signals from the lipid membranes 14-1, . . . , 14-8 of the taste sensor array 13 are supplied as 8-channel signals to buffer amplifiers 19-1, . . . , 19-8 via lead wires 17-1, . . . , 17-8, respectively. Outputs from the buffer amplifiers 19 are selected by an analog switch (8 channels) 20 and loaded to an A/D converter 21. An electrical signal from the reference electrode 15 is also supplied as a reference potential to the A/D converter 21 via a lead wire 18. A difference between the reference potential and a potential from the membrane is converted into a digital signal. This digital signal is subjected to predetermined data processing by a micro computer 22 and displayed by an X-Y recorder 23.

Since the measuring system is illustrated as a system for measuring a membrane potential, a portion for containing the solution to be measured is covered with a conductive material to obtain a ground potential 24 in consideration of especially setting of the reference potential. In this case, the reference electrode 15 may be connected to the ground potential as shown with dashed line. Note that the micro computer 22 may perform, as control of the overall measuring system, pre-processing in step ST1, measuring processing in step ST2, and data processing in step ST3 in FIG. 7B.

In the taste sensor of this type, a measuring system for measuring a conductivity or self-excited oscillation of a lipid membrane can be arranged similarly to that shown in FIG. 7A. In the taste sensor of this type, however, measurement of a membrane potential is basic and important. Therefore, the measurement results of the membrane potential will be described below, and description of other measuring systems will be omitted.

[Measurement Result (a), Potential of Resting State]

Firstly, a potential of a resting state was measured to check whether the potential of the taste sensor using lipid membranes as shown in FIGS. 5, 6A, and 6B was stationary. In the measuring system as shown in FIG. 7A, an aqueous sodium chloride solution having a concentration of 10 m mole/l was used as a solution to be measured, and measurement was performed every five minutes for two hours. As a result, it was found that a stable potential was obtained on the order of ten minutes for a taste sensor having lipid membranes using any lipid molecule listed in Tables 1 and 2. Therefore, it was confirmed that a stable signal could be obtained.

A time period on the order of ten minutes, if longer, 30 minutes, and if shorter, five minutes required before stabilization was obtained is assumed to be an elapse time before a slight bias current of the buffer amplifier 19 is stabilized. In any case, this time period is not essentially derived from the lipid membrane.

[Measurement Result (b), Potential Response to Various Taste Substances (I)]

Potential responses of the taste sensors using various lipid membranes to the five basic taste substances enumerated above were checked.

An aqueous solution of each taste substance having a concentration of 0.01 m mole/l was used as a start solution to measure a potential difference with respect to the reference electrode in ten minutes after the taste substance was dropped. Thereafter, a taste substance having a higher concentration was dropped to increase the concentration of the solution, and a potential difference with respect to the reference electrode was measured five minutes after the taste substance was dropped (i.e., after stabilization was obtained) for each concentration of 0.01, 0.03, 0.1, 0.3, 1.3, 3, 10, 30, and 100 m mole/l (note that the concentration of quinine hydrochloride as a bitter substance was limited to 10 m mole/l in consideration of its solubility). The measurement results are summarized in FIGS. 8 to 15. In FIGS. 8 to 15, lipid molecules of the lipid membranes used as the taste sensor are as follows. As the plasticizer, tricresyl phosphate (TCP) was used, in all cases of FIGS. 8 to 15.

FIG. 8: oleic acid

FIG. 9: DOAB

FIG. 10: decylalcohol

FIG. 11: n-octadecylchloride

FIG. 12: dioctylphosphate

FIG. 13: cholesterol

FIG. 14: TOMA

FIG. 15: oleylamine

In each of FIGS. 8 to 15, the type of line corresponds to the type of taste substance, the ordinate represents a membrane potential change in units of my, and the abscissa represents the concentration of each taste substance.

FIGS. 16 and 17 show the measurement results shown in FIGS. 8 to 15 in different aspects. A difference between FIGS. 16 and 17 is that FIG. 16 is a bar graph and FIG. 17 is a graph in which peaks of the bars shown in FIG. 16 are connected in the abscissa direction. In FIGS. 16 and 17, the ordinate represents a membrane potential change in units of mV, and the abscissa represents the type of lipid molecule forming each lipid membrane. The bar graph represents a potential change corresponding to the concentration which human easily can discriminate a taste for each taste substance (whose concentration is shown in FIG. 16), and is obtained in FIGS. 8 to 15. As is apparent from FIGS. 16 and 17, the pattern of an output from the lipid membrane array with respect to the five basic tastes is different among the five tastes.

The characteristics obtained from the above measurement results are as follows.

(a) n-octadecylchloride and decylalcohol similarly respond.

(b) DOAB appears to be similar to decylalcohol.

(c) Oleic acid is also similar to decylalcohol.

(d) Behaviors of lipids having polar groups bonded to carbon atoms are similar to each other.

(e) A taste sensor using TOMA exhibits the same curve for sourness, saltiness, and bitterness. Since any of these taste substances have $Cl^-$, this sensor serves as a $Cl^-$-ion sensor.

(f) Unlike other lipid membranes, oleylamine has a feature which responds with opposite polarities to bitterness and sourness.

(g) Dioctylphosphate contains a phosphoric acid group and an unsaturated carbon bonding and has a structure similar to that of DOPH described above with reference to the related art. Dioctylphosphate responds similarly to DOPH, e.g., is very sensitive to bitterness. In addition, a response of dioctylphosphate to sourness is stronger than that to saltiness. It is assumed that this suggests an effect of $H^+$ ions.

The characteristics of the lipid membranes viewed from the taste substances are as follows.

(a) Sourness and bitterness have similar relationships with respect to each lipid (symbols □ and ◇ in FIG. 17).

Sourness and bitterness can be distinguished from each other by using a difference between the polarities of oleylamine.

(b) A response of each lipid membrane except for dioctylphosphate, similarly changes with respect to Umami and sweetness, and a response similar to that of a human tongue is observed.

(c) A polarity pattern of sweetness is opposite to that of sourness or saltiness. This suggests that a lipid membrane also has a phenomenon in which human feels sweetness as deliciousness.

Figure 27:
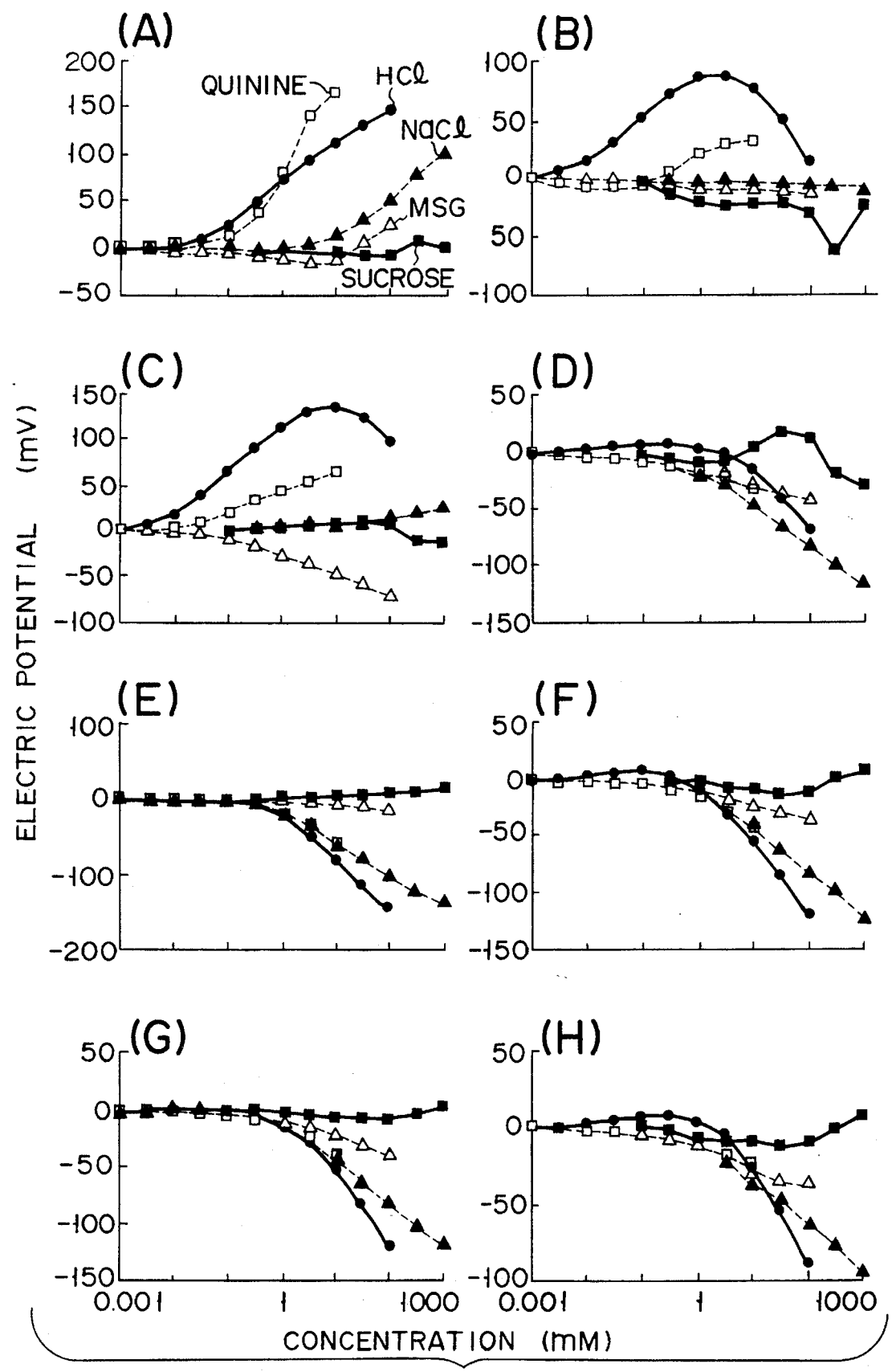
Figure 29:
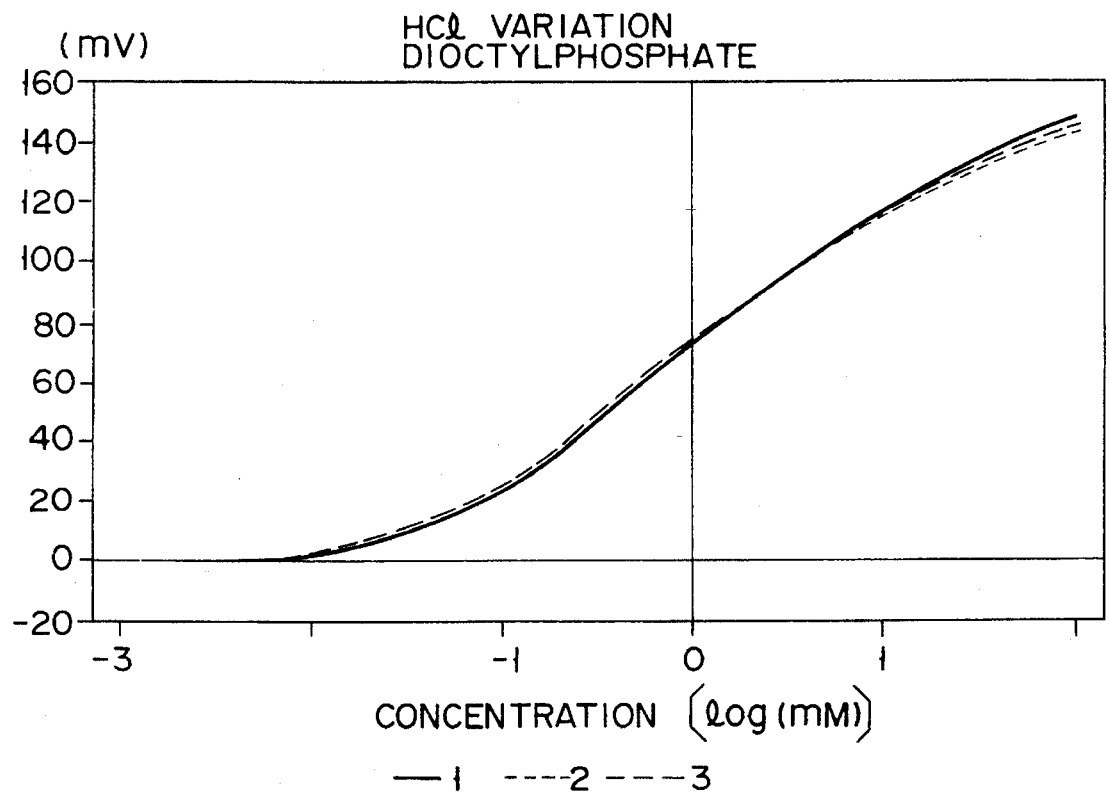
Figure 30:
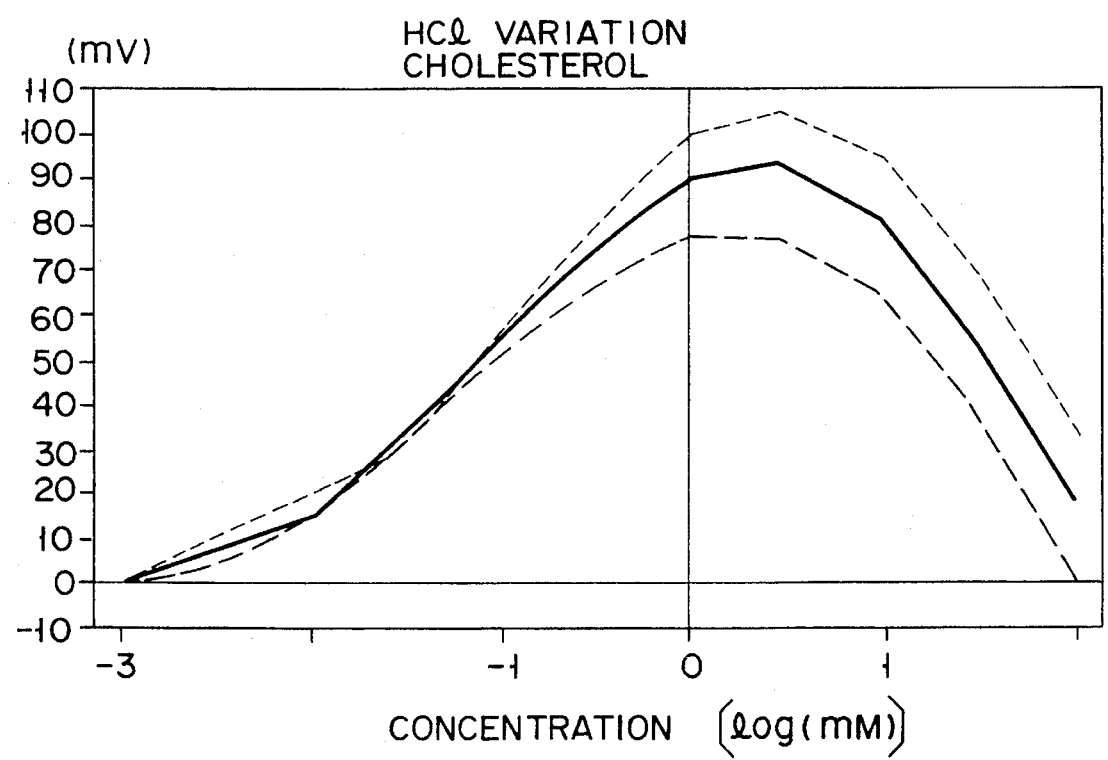

Referring to FIG. 27, (a) to (h) represent response characteristics of an 8-channel taste sensor array using a plurality of different lipid membranes (a) to (h) with respect to the five basic taste substances. Lipid molecules of the lipid membranes in the channels (a) to (h) are as follows. As the phasticizer, dioctylphenylphosphonate (DOPP) was used, in all channels (a) to (h).

(a): dioctylphosphate ($2C_8POOH$)

(b): cholesterol (c): oleic acid (d): decylalcohol (e): trioctylmethylammoniumchloride (TOMA)

(f): oleylamine (g): distearyldimethylammoniumbromide (h): trimethylstearylammoniumchloride Two types of response threshold values can be adopted for this sensor array. One is a response threshold value, and the other one is a threshold value at which a taste can be recognized. If a potential of at least one sensor channel changes, a response is determined, and a concentration at this time is defined as the response threshold value. At this threshold value, human cannot recognize a taste but feels a stimulus. As is apparent from FIG. 27, the threshold values are 1 μM, 0.1 mM, 10 μM, 10 mM, and 10 μM for HCl, NaCl, quinine, sucrose, and MSG, respectively.

A point at which a correlation coefficient between a pattern shown in FIG. 28 and a response pattern of a certain concentration exceeds, e.g., 0.7 is taken as a concentration at which a taste can be recognized. These concentration values are 9 μM, 0.25 mM, 60 μM, 160 mM, and 80 μM for HCl, NaCl, quinine, sucrose, and MSG, respectively.

The threshold values are also different in human between determination of "whether a specific taste is sensed" and "whether any taste is sensed". Also, the threshold value largely changes in accordance with a method or a data processing method in a sensory test.

According to C. Pfaffman, "Handbook of Physiology", Sec. 1, Neurophysiology Vol. 1, ed. by J. Field, American Physiological Society, Washington D.C. 1959, p. 507, threshold values in human are 900 μM, 10 mM, 8 μM, and 10 mM for HCl, NaCl, quinine, and sucrose, respectively.

The threshold values of the present invention are slightly different from but substantially coincide with those reported in the above reference. This means that the taste sensor of the present invention can replace the five taste sense of human.

[Measurement Result (c), Potential Response to Various Taste Substances (II)]

Measurement results to the mixture of lipid membranes as $2C_8POOH+\alpha$, as listed in Table 2 are summarized as following.

(a) NaCl

NaCl response is strong in a membrane consisting of only dioctylphosphate and suppressed by mixing cholesterol. Almost no change was found in a membrane in which DOAB or lecithin was mixed, but a response was decreased by simultaneously mixing both the substances. D-100 has a maximum value of the response, and C-10 and C.L-20 have minimum values of the response for 10 m mole/l and 100 m mole/l, respectively.

(b) HCl response is strong in a membrane in which lecithin is mixed, and is suppressed by mixing cholesterol. Almost no influence is found in response by mixing DOAB. L-10 has a maximum value of the response, and C-20 has a minimum value of the response.

(c) Quinine

Quinine response is strong in a membrane in which cholesterol is mixed but suppressed by mixing DOAB or lecithin. In particular, although no change is found by mixing only lecithin, a significant suppression effect is found when lecithin is mixed together with cholesterol. Similarly, a response is suppressed when DOAB and lecithin are contained. C-20 and D-100 have maximum values of the response for 0.1 m mole/l and 1 m mole/l, respectively, and N.L-15 has a minimum value of the response.

(d) Sucrose

Sucrose response is enhanced when DOAB is mixed (N-5), and this effect significantly appears especially when DOAB is mixed together with cholesterol (NC-15). The response is suppressed by mixing lecithin (C.L-20). N.C-15 has a maximum value of the response, and C.L-20 has a minimum value of the response.

As described above, a large difference is present between responses of lipid membranes in accordance with the type of taste substances.

Figure 18:
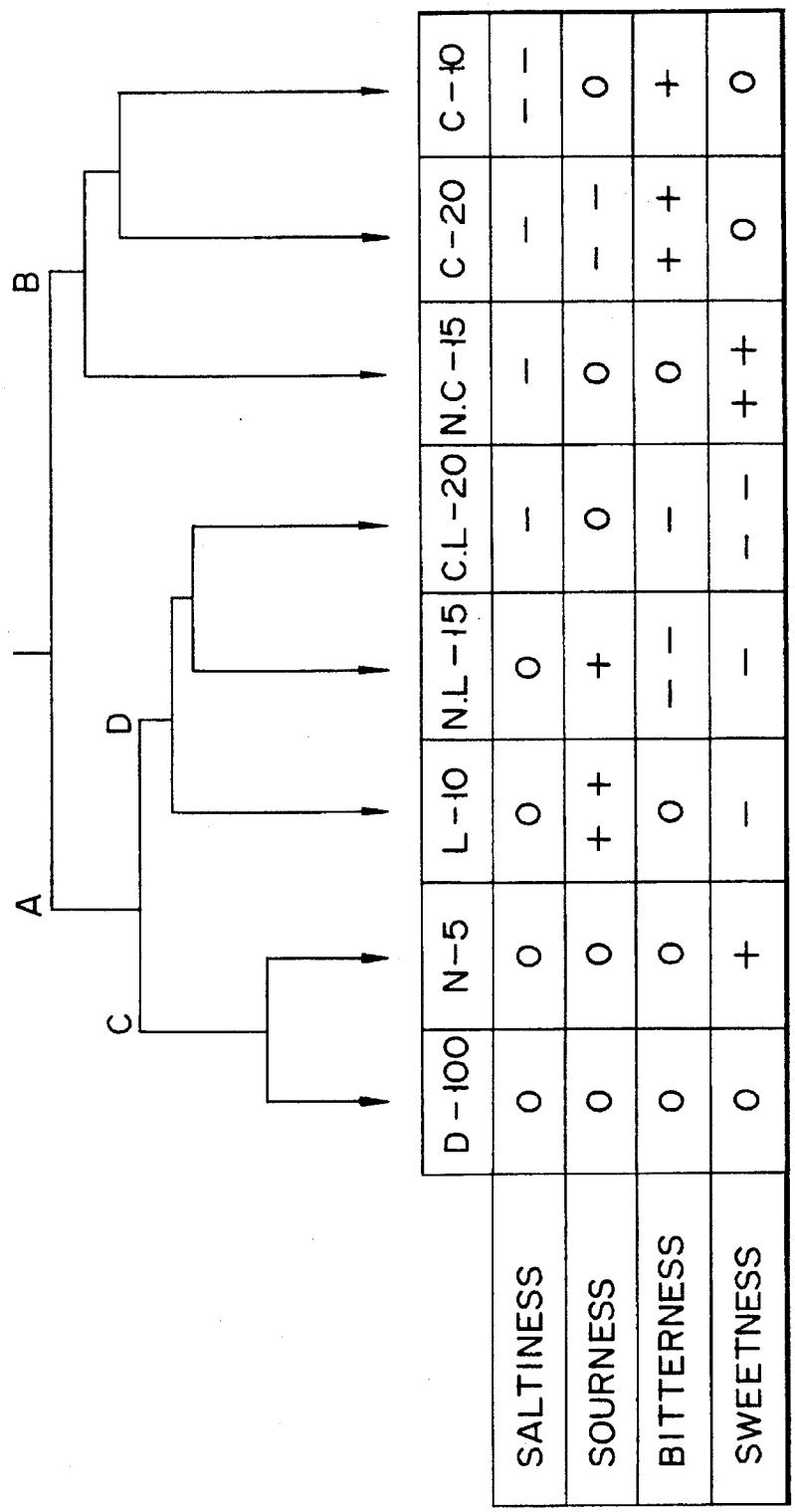
FIG. 18 is a view showing a dendrogram obtained by data analysis performed by the taste sensor of the present invention.
Figure 21A:
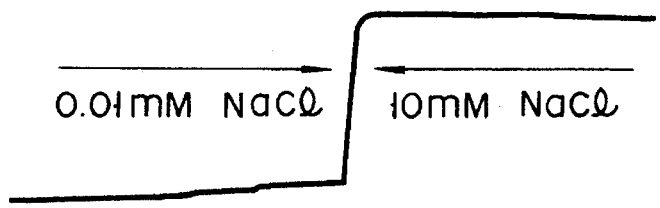
FIGS. 21A to 21D to 24A to 24D are graphs showing transient responses corresponding to saltiness, sourness, bitterness, and sweetness of various types of lipid membranes for use in the taste sensor of the present invention.
Figure 21B:
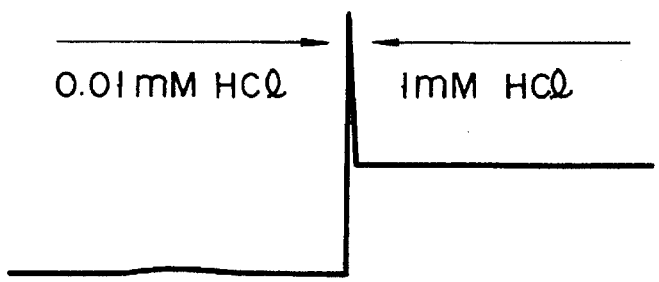
Figure 21C:
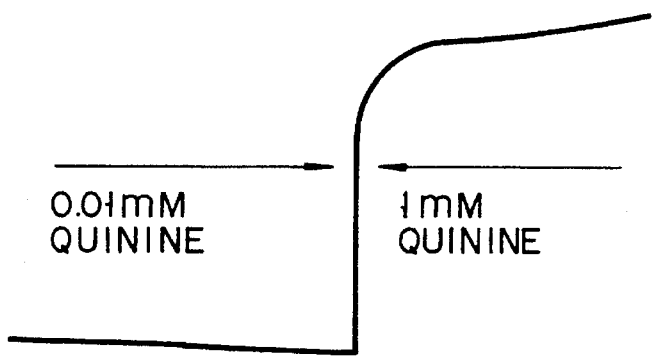
Figure 21D:
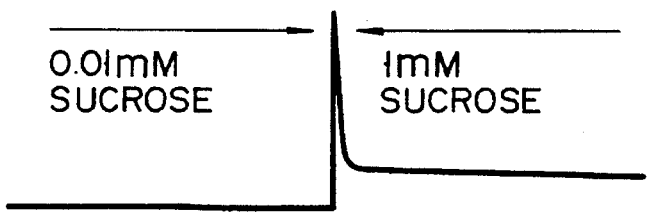
Figure 22A:
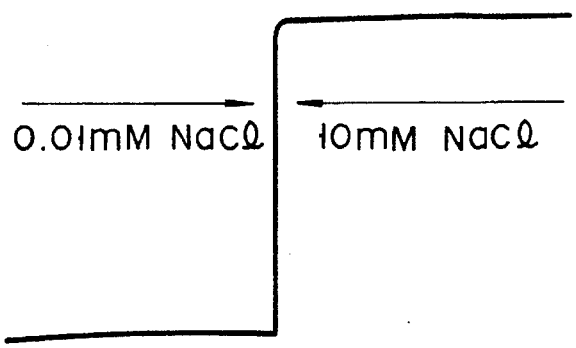
Figure 22B:
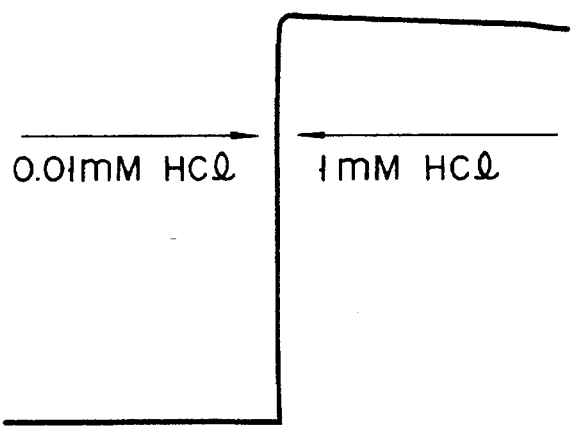
Figure 22C:
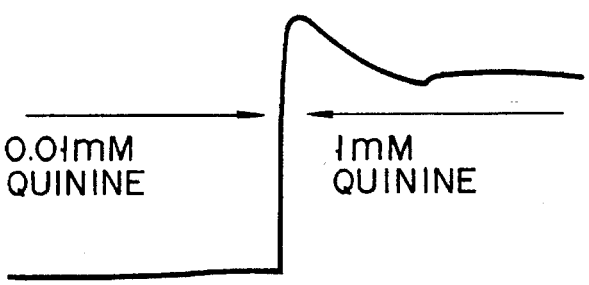
Figure 22D:
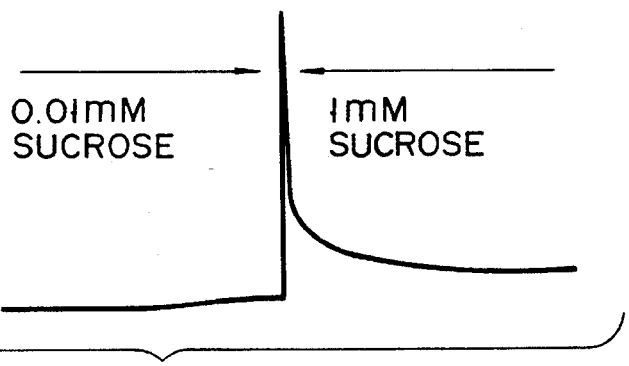
Figure 23A:
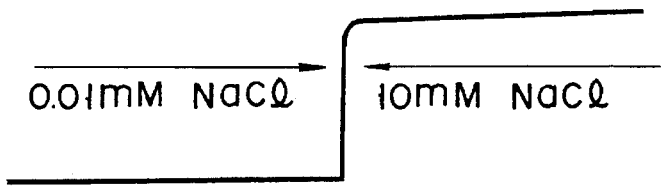
Figure 23B:
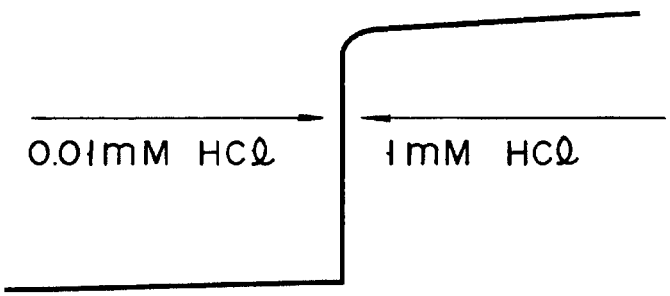
Figure 23C:
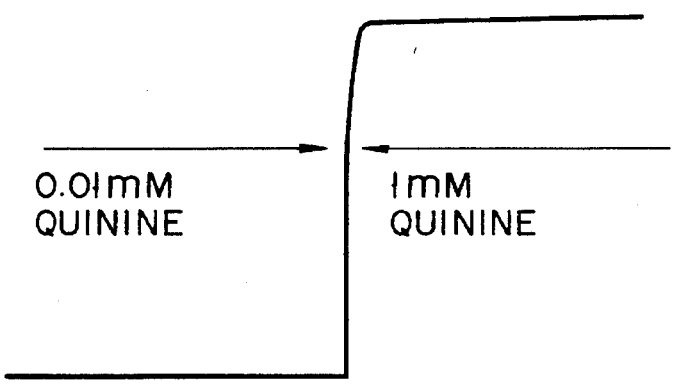
Figure 23D:
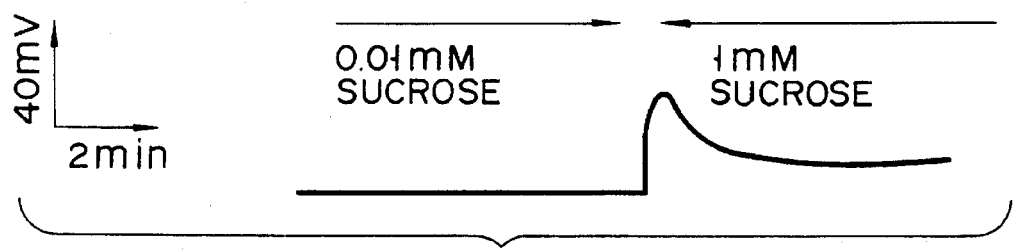
Figure 24A:
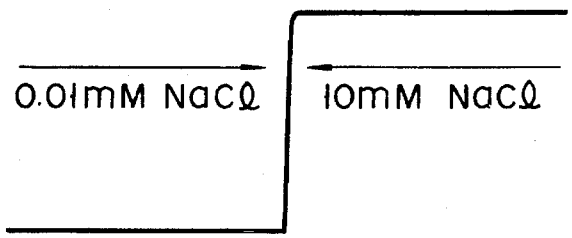
Figure 24B:
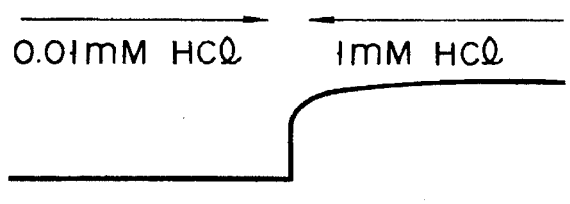
Figure 24C:
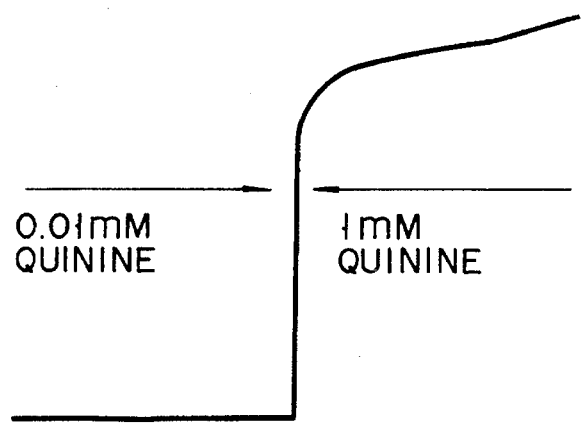
Figure 24D:
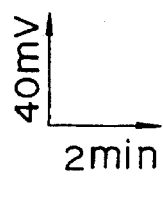
Figure 25:
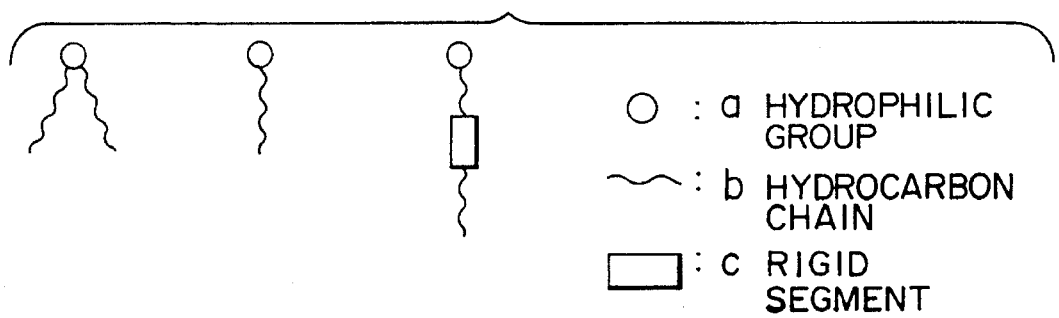
FIG. 25 is a schematic view showing lipid molecules for explaining the related art.

In order to examine a similarity of each lipid membrane with respect to a taste response, analysis was performed in accordance with cluster analysis as a method of multivariate analysis. Each of eight types of lipid membranes was considered as an individual, and a taste substance response of each membrane was considered as a characteristic of the individual. Used data was a potential change of each membrane for NaCl of 10 m mole/l HCl of 0.1 m mole/l quinine of 0.1 m mole/l and sucrose of 1 m mole/l. A standard Euclidean distance was adopted as a distance between the individuals, and a minimum distance method was used as a distance between clusters. FIG. 18 shows a dendrogram obtained by analysis.

Referring to FIG. 18, closer individuals are grouped in an earlier stage to form a cluster. As is apparent from FIG. 18, the lipid membranes are divided into A and B groups, and the A group is subdivided into C and D groups. The B group consists of lipid membranes in which cholesterol is mixed except for a membrane of C.L-20, and the A group includes the other lipid membranes. This implies that a membrane structure changes somewhat since cholesterol has a large hydrophobic group and this lipid membrane has characteristics different from those of the other lipid membranes.

Similarly, the D group is influenced by lecithin. The C group includes D-100 and N-5, and the characteristics of the two groups are similar with respect to a taste response. That is, an influence of DOAB is absorbed by characteristics of the other lipid component. This is the same as for N.L-15 and N.C-15. From these facts, it is apparent that the characteristics of a lipid membrane are largely changed by lecithin or cholesterol. As shown in the measurement results, a difference is present between taste response characteristics of D-100 and N-5, e.g., a membrane in which DOAB is mixed responds to sweetness more easily. That is, the characteristics of a lipid membrane are sufficiently changed upon mixing of each lipid and are stabilized by the mixed lipid. Such a difference is not expressed in cluster analysis.

[Measurement Result (d), Potential Response to Beverages (I)]

FIG. 19 shows results of a membrane potential response to various types of coffee. Referring to FIG. 19, the abscissa indicates the lipid membranes listed in Table 2, and the ordinate indicates a normalized potential change from a reference potential in a KCl solution having a concentration of 10 m mole/l.

FIG. 19 shows normalized response patterns in which data is considered as an eight-dimensional vector and a vector length is normalized with respect to 1 on the basis of a concept that not the magnitude of a response pattern but a difference between the patterns corresponds to a taste. For comparison, a pattern with respect to quinine which is a typical substance eliciting bitterness is also shown in the graph.

Since response patterns to coffee are very similar to a response pattern to quinine except for N-5, C-10, and C-20, it can be determined that a main taste of coffee is bitterness. It is very interesting that the response pattern to coffee is similar to that to quinine which is a bitter substance although the bitterness of coffee is mainly obtained by caffeine and tannin but not depend to quinine.

Response patterns of each of N-5, C-10, and C-20 are different between coffee and quinine because caffeine or tannin which is a bitter substance different from quinine is present or another substance different from a bitter substance is mixed in coffee.

When response patterns to regular coffee (blue mountain, mocha, and brazil) are compared with those to instant coffee, normalized potential changes with respect to instant coffee are larger than those to regular coffee in N-5 and C.L-20, and normalized potential changes with respect to instant coffee are smaller than those to regular coffee in C-20 and N.C-15.

Regular coffee and instant coffee can be distinguished from each other by this difference.

Three types of regular coffee will be considered next. Normalize potential changes with respect to blue mountain are larger than those with respect to the other two types in D-100 but smaller than those to the other two types in L-10. This characteristic is similar to that of saltiness. L-10 strongly responds to both mocha and brazil, and this indicates the characteristic of sourness. Since, however, a normalized potential change with respect to brazil is smaller than that with respect to mocha in D-100, the two types of coffee can be distinguished from each other. As described above, differences are found in response patterns between the three types of regular coffee.

Although it is not obvious that these differences directly lead to taste differences of human, it is assumed that the fact at least has some meaning with respect to taste.

[Measurement Result (e), Potential Response to Beverages (II)]

FIG. 20 shows results of membrane potential responses with respect to liquors. In FIG. 20, the abscissa and the ordinate are the same as those in FIG. 19. These membrane responses are normalized similarly to those with respect to coffee.

The response patterns shown in FIG. 20 are similar to a response pattern with respect to sucrose since a response is strong in a lipid membrane containing DOAB and is suppressed in a lipid membrane containing lecithin. This phenomenon significantly appears with respect to Japanese sake. This is because brewing sugars were contained in Japanese sake used in the experiments.

In addition, it is assumed that the similar response patterns are obtained as a whole since an effect of alcohol is strong. A slight difference of a response pattern is found with respect to beer especially in C-10. A difference between white and red wine is small. A pattern with respect to Japanese sake is different from those with respect to wine and beer.

In this experiment, wine and beer were measured at room temperature, and carbonic acid was removed from beer. Therefore, the tastes of these liquors might be different from their original ones, however, since differences are found between response patterns with respect to wine, Japanese sake, and beer, it is assumed that identification of a taste and discrimination between types of beverages can be performed by using these differences.

[Measurement Result (f), Transient Response to Tasted Substances]

Transient responses of four samples (D-100, N-5, C-10, and L-10) of the lipid membranes listed in Table 2 were measured. The results are shown in FIGS. 21A to 24D in which the abscissa indicates a time and the ordinate indicates a membrane potential. A taste substance and a concentration of an aqueous solution are shown in each measurement waveform. A relationship between the drawings and the samples, i.e., the lipid membranes (see Table 2) is as follows:

In each drawing, suffix characters A, B, C, and D correspond to saltiness, sourness, bitterness, and sweetness, respectively.

As the concentration changes from low to high, a membrane potential abruptly changes in a depolarizing direction and settles at a predetermined value in about five minutes. Since the concentration was changed by dropping a high-concentration solution into a solution to be measured in this measuring system, it is difficult to assume that a change in a very initial stage is a specific transient response with respect to only a taste substance.

However, obvious differences are found between response patterns with respect to various types of taste substances except for such a response in a very initial stage. NaCl causes a similar rapid change in any membranes. HCl causes a moderate change subsequently to an initial rapid change in C-10 and L-10. Quinine causes a moderate change subsequently to an initial rise except for C-10. Sucrose causes a moderate change except for D-100.

It is assumed that such a dynamic change in response speed or the like can be obtained by adding information concerning a taste substance to a time axis of a surface potential change.

Therefore, information in a number more than the number of channels can be obtained from the multi-channel array taste sensor according to the present invention.

[Measurement Result (g), Reproducibility]

In order to evaluate a reproducibility of the taste sensor according to the present invention, three taste sensors (denoted by reference numerals 1, 2, and 3 in each drawing) were prepared for each of various types of lipid membranes. FIGS. 29 to 36 show variations in response characteristics of the sensors with respect to sourness.

As is apparent from FIGS. 29 to 36, although large variations are more or less found in membranes including cholesterol and decyl alcohol, variations are small in other membranes, and almost no variations are found in membranes consisting of dioctylphosphate, TOMA, oleylamine, and DOAB to indicate superiority of these membranes. This indicates that the taste sensor according to the present invention has a valuable reproducibility.

As has been described above, according to the taste sensor of the present invention, a membrane is formed by using a lipid which is a main constituting component of a taste receptor membrane as a base material, and electrical characteristics of the membrane are detected. Therefore, the taste sensor has a function close to that of the sense of taste of human.

Since the lipid membrane is formed by mixing a polymer material having a matrix structure on its surface therein, the taste sensor can be easily brought into contact with food as an object to be examined. In addition, a stable output signal and reproducible data can be obtained from the taste sensor, and the taste sensor can be repetitively used for a long time period.

Furthermore, since the type of lipid molecule of the lipid membrane for use in the taste sensor of the present invention can be changed, umami can be evaluated in addition to the four basic tastes, saltiness, sourness, sweetness, and bitterness.

Moreover, according to the taste sensor of the present invention, although a plurality of types of sensors are influenced on a combined effect of tastes, respectively, a plurality of types of lipid molecules are used in lipid membranes, thereby obtaining multi-channel electrical signals to be detected. Therefore, not simple addition of outputs concerning the basic tastes but a taste obtained by a combined effect such as a synergistic effect or a suppression effect of the basic tastes can be detected.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. A taste sensor which is capable of determining qualitative changes in a sample having a known sense of taste, said taste sensor comprising:

a lipid membrane for reacting with the sample to induce a change in electrical characteristics corresponding to the qualitative changes in the sample, said lipid membrane including:

a) lipid molecules having a hydrophobic portion in which an atomic array extends in the longitudinal direction and a hydrophilic portion present at a portion of said atomic array extending in the longitudinal direction: and b) a membrane-forming material mixed with said lipid molecules and having a matrix structure for supporting said lipid molecules on a surface thereof, said membrane-forming material being made of a polymer, at least some of said lipid molecules being supported in the matrix structure of said membrane-forming material such that said hydrophilic portion is arranged on the surface, and said change in the electrical characteristics being induced in accordance with a change in electrical characteristics of said lipid membrane, when the sample reacts with said lipid molecules arranged at least essentially on the surface of said lipid membrane;

signal input means for inputting a signal in accordance with said change in the electrical characteristics induced by said lipid membrane; and signal processing means for processing the signal input by said signal input means, thereby determining the qualitative changes in the sample having the known sense of taste.

2. A taste sensor according to claim 1, wherein said lipid molecules include a saturated hydrocarbon group and at least one of a phosphilic acid group, an amino group, an ammonium group, a hydroxyl group, and a carboxyl group.

3. A taste sensor according to claim 1, wherein said membrane-forming material is made of a mixture including a polymer and a plasticizer.

4. A taste sensor according to claim 3, wherein said lipid molecules include a saturated hydrocarbon group and at least one of a phosphilic acid group, an amino group, an ammonium group, a hydroxyl group and a carboxyl group.

5. A taste sensor according to claim 1, wherein said lipid membrane is mounted on an electrode formed in a base material.

6. A taste sensor according to claim 5, wherein said lipid membrane is in contact with said electrode via a buffer layer.

7. A method of manufacturing a lipid membrane used in a taste sensor which is capable of determining qualitative changes in a sample having a known sense of taste, said method comprising the steps of:

preparing a lipid material having a hydrophobic portion in which an atomic array extends in the longitudinal direction and a hydrophilic portion present at a portion of the atomic array extending in the longitudinal direction;

preparing a membrane-forming material made of a polymer material;

mixing and dissolving said lipid material and said membrane-forming material, at a predetermined mixing ratio, by adding a solvent required by said polymer material, thereby obtaining an essentially homogeneous mixture;

shallowing the essentially homogeneous mixture, so as to form a thin membrane including the solvent;

volatilizing the solvent in the thin membrane, thereby forming a lipid membrane, said lipid membrane inducing a change in electrical characteristics corresponding to the qualitative changes in the sample when the sample interacts with the surface of said lipid membrane; and dipping said liquid membrane into an aqueous solution of at least one type of an electrolyte, thereby improving the sensitivity of said lipid membrane.

8. The method according to claim 7, wherein said lipid molecules include a saturated hydrocarbon and at least one of a phosphoric acid group, an amino group, an ammonium group, a hydroxyl group, and a carboxyl group.

9. A lipid membrane in a taste sensor which is capable of determining qualitative changes in a sample having a known sense of taste, said lipid membrane comprising:

lipid molecules having a hydrophobic portion in which an atomic array extends in the longitudinal direction and a hydrophilic portion present at a portion of said atomic array extending in the longitudinal direction; and a membrane-forming material mixed with said lipid molecules and having a matrix structure for supporting said lipid molecules on a surface thereof, said membrane-forming material being made of a polymer, at least some of said lipid molecules being supported in the matrix structure of said membrane-forming material such that said hydrophilic portion is arranged on the surface, and said change in the electrical characteristics being induced in accordance with a change in electrical characteristics of said lipid membrane, when the sample reacts with said lipid molecules arranged at least essentially on the surface of said lipid membrane, wherein the surface of said lipid membrane has regions where at least one of said lipid molecules is supported in the matrix structure, thereby mixing the polymer and said lipid molecules.

10. A lipid membrane according to claim 9, wherein said lipid molecules include a saturated hydrocarbon group and at least one of a phosphilic acid group, an amino group, an ammonium group, a hydroxyl group, and a carboxyl group.

11. A lipid membrane according to claim 9, wherein said membrane-forming material is made of a mixture including a polymer and a plasticizer.

12. A lipid membrane according to claim 11, wherein said lipid molecules include a saturated hydrocarbon group and at least one of a phosphilic acid group, an amino group, an ammonium group, a hydroxyl group and a carboxyl group.

13. A method of manufacturing a lipid membrane used in a taste sensor which is capable of determining qualitative changes in a sample having a known sense of taste, said method comprising the steps of:

preparing a lipid material having a hydrophobic portion in which an atomic array extends in the longitudinal direction and a hydrophilic portion present at a portion of the atomic array extending in the longitudinal direction;

preparing a membrane-forming material made of a polymer material;

mixing and dissolving said lipid material and said membrane-forming material, at a predetermined mixing ratio, by adding a solvent required by said polymer material, thereby obtaining an essentially homogeneous mixture;

shallowing the essentially homogeneous mixture, so as to form a thin membrane including the solvent;

volatilizing the solvent in the thin membrane, thereby forming a lipid membrane, said lipid membrane inducing a change in electrical characteristics corresponding to the qualitative changes in the sample when the sample interacts with the surface of said lipid membrane; and dipping said lipid membrane into an aqueous solution of an electrolyte, thereby preserving said lipid membrane.

14. The method according to claim 13, wherein said lipid molecules include a saturated hydrocarbon and at least one of a phosphoric acid group, an amino group, an ammonium group, a hydroxyl group, and a carboxyl group.

* * * * *